United States Patent
Furutani et al.

(10) Patent No.: US 9,617,563 B2
(45) Date of Patent: Apr. 11, 2017

(54) RECOMBINANT CELL, AND METHOD FOR PRODUCING β-PHELLANDRENE

(71) Applicants: SEKISUI CHEMICAL CO., LTD., Osaka (JP); TOHOKU UNIVERSITY, Miyagi (JP)

(72) Inventors: Masahiro Furutani, Tokyo (JP); Akihiro Uenishi, Tsukuba (JP); Koichiro Iwasa, Tokyo (JP); Yasuyuki Kori, Isesaki (JP); Seiji Takahashi, Sendai (JP); Takefumi Shimoyama, Sendai (JP)

(73) Assignees: TOHOKU UNIVERSITY, Miyagi (JP); SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/429,510

(22) PCT Filed: Sep. 19, 2013

(86) PCT No.: PCT/JP2013/075282
§ 371 (c)(1),
(2) Date: Mar. 19, 2015

(87) PCT Pub. No.: WO2014/046174
PCT Pub. Date: Mar. 27, 2014

(65) Prior Publication Data
US 2015/0218589 A1    Aug. 6, 2015

(30) Foreign Application Priority Data

Sep. 21, 2012  (JP) ................... 2012-208292
Jun. 6, 2013   (JP) ................... 2013-119612

(51) Int. Cl.
| | |
|---|---|
| *C12P 5/00* | (2006.01) |
| *C12N 1/20* | (2006.01) |
| *C12N 15/00* | (2006.01) |
| *C12N 1/14* | (2006.01) |
| *C12N 9/10* | (2006.01) |
| *C12N 9/88* | (2006.01) |
| *C07H 21/04* | (2006.01) |
| *C12N 15/52* | (2006.01) |
| *C12N 9/00* | (2006.01) |

(52) U.S. Cl.
CPC ............ *C12P 5/007* (2013.01); *C12N 9/00* (2013.01); *C12N 9/1085* (2013.01); *C12N 9/88* (2013.01); *C12N 15/52* (2013.01); *C12Y 205/01001* (2013.01); *C12Y 205/01028* (2013.01); *C12Y 402/03051* (2013.01)

(58) Field of Classification Search
CPC .......... C12N 9/88; C12N 9/1085; C12P 5/007
See application file for complete search history.

(56) References Cited

U.S. PATENT DOCUMENTS

| | | | | |
|---|---|---|---|---|
| 7,622,282 | B2* | 11/2009 | Keasling | C12N 9/1205 435/132 |
| 2002/0102690 | A1 | 8/2002 | Cheng et al. | |
| 2009/0137014 | A1 | 5/2009 | Tsuruta et al. | |

FOREIGN PATENT DOCUMENTS

| | | |
|---|---|---|
| JP | 2000-245482 | 9/2000 |
| JP | 2005-500805 | 1/2005 |
| JP | 2010-539902 | 12/2010 |
| WO | 2009/036067 | 3/2009 |
| WO | 2013/119644 | 8/2013 |

OTHER PUBLICATIONS

Branden et al. Introduction to Protein Structure, Garland Publishing Inc., New York, p. 247, 1991.*
Bouvier et al. Molecular cloning of geranyl diphosphate synthase and compartmentation of monoterpene synthesis in plant cells. Plant J. 24:241-252(2000).*
International Search Report issued Oct. 29, 2013 in International (PCT) Application No. PCT/JP2013/075282.
Z. A. Demissie et al., "Cloning and Functional Characterization of β-Phellandrene Synthase from *Lavandula angustifolia*", Planta, vol. 233, pp. 685-696, 2011.
A. L. Schilmiller et al., "Monoterpenes in the Glandular Trichomes of Tomato are Synthesized from a Neryl Diphosphate Precursor rather than Geranyl Diphosphate", Proceedings of the National Academy of Sciences, vol. 106, No. 26, pp. 10865-10870, Jun. 30, 2009.
Arabidopsis Thaliana mRNA for Geranyl Diphosphate Synthase, Nov. 22, 2000, online, GenBank Accession No. Y17376.
Solanum Lycopersicum Cultivar M82 Neryl Diphosphate Synthase 1 (NDPS1) mRNA, Complete cds, Jul. 8, 2009, online, retrieved on Oct. 4, 2013, GenBank Accession No. FJ797956.
Solanum Lycopersicum Cultivar M82 Terpene Synthase 1 (PHS1) mRNA, Complete cds, Jul. 8, 2009, online, retrieved on Oct. 4, 2013, GenBank Accession No. FJ797957.
Lavandula Angustifolia Cultivar Lady Beta-Phellandrene Synthase mRNA, complete cds, Jan. 9, 2011, online, retrieved on Oct. 4, 2013, GenBank Accession No. HQ404305.

(Continued)

*Primary Examiner* — Yong Pak
(74) *Attorney, Agent, or Firm* — Wenderoth, Lind & Ponack, L.L.P.

(57) ABSTRACT

To provide a series of techniques for obtaining β-phellandrene with high purity and in a large quantity.
Provided is a recombinant cell capable of producing β-phellandrene, prepared by introducing at least one nucleic acid selected from the group consisting of a nucleic acid encoding geranyl pyrophosphate (GPP) synthase and a nucleic acid encoding neryl pyrophosphate (NPP) synthase, and a nucleic acid encoding β-phellandrene synthase into a host cell in such a manner that these nucleic acids are expressed in the host cell. Also provided is a method for producing β-phellandrene by culturing the recombinant cell to produce β-phellandrene in the recombinant cell.

14 Claims, 2 Drawing Sheets

(56) References Cited

OTHER PUBLICATIONS

K. Satoh et al., "Biomass-Derived Heat-Resistant Alicyclic Hydrocarbon Polymers: Poly(Terpenes) and their Hydrogenated Derivatives", Green Chemistry, vol. 8, pp. 878-882, 2006.
K. Mori, "Synthesis of (1$S$,4$R$)-4-Isopropyl-1-Methyl-2-Cyclohexen-1-ol, the Aggregation Pheromone of the Ambrosia Beetle *Platypus quercivorus*, Its Racemate, (1$R$,4$R$)- and (1$S$,4$S$)-Isomers", Tetrahedron Asymmetry, vol. 17, pp. 2133-2142, 2006.
English Translation of International Preliminary Report on Patentability and Written Opinion issued in corresponding International Application No. PCT/JP2013/075282 on Mar. 24, 2015.
Supplementary European Search Report dated Mar. 15, 2016 issued in parallel European Patent Application No. EP 13838825.

* cited by examiner

Retention time (min)

SEQUENCE LISTING

```
<160> NUMBER OF SEQ ID NOS: 30

<210> SEQ ID NO 1
<211> LENGTH: 1269
<212> TYPE: DNA
<213> ORGANISM: Arabidopsis thaliana
<220> FEATURE:
<221> NAME/KEY: CDS
<222> LOCATION: (1)..(1269)
<223> OTHER INFORMATION:

<400> SEQUENCE: 1 atg tta ttc acg agg agt gtt gct cgg att tct tct aag ttt ctg aga    48
Met Leu Phe Thr Arg Ser Val Ala Arg Ile Ser Ser Lys Phe Leu Arg
1               5                   10                  15 aac cgt agc ttc tat ggc tcc tct caa tct ctc gcc tct cat cgg ttc    96
Asn Arg Ser Phe Tyr Gly Ser Ser Gln Ser Leu Ala Ser His Arg Phe
            20                  25                  30 gca atc att ccc gat cag ggt cac tct tgt tct gac tct cca cac aag   144
Ala Ile Ile Pro Asp Gln Gly His Ser Cys Ser Asp Ser Pro His Lys
        35                  40                  45 ggt tac gtt tgc aga aca act tat tca ttg aaa tct ccg gtt ttt ggt   192
Gly Tyr Val Cys Arg Thr Thr Tyr Ser Leu Lys Ser Pro Val Phe Gly
    50                  55                  60 gga ttt agt cat caa ctc tat cac cag agt agc tcc ttg gtt gag gag   240
Gly Phe Ser His Gln Leu Tyr His Gln Ser Ser Ser Leu Val Glu Glu
65                  70                  75                  80 gag ctt gac cca ttt tcg ctt gtt gcc gat gag ctg tca ctt ctt agt   288
Glu Leu Asp Pro Phe Ser Leu Val Ala Asp Glu Leu Ser Leu Leu Ser
                85                  90                  95 aat aag ttg aga gag atg gta ctt gcc gag gtt cca aag ctt gcc tct   336
Asn Lys Leu Arg Glu Met Val Leu Ala Glu Val Pro Lys Leu Ala Ser
            100                 105                 110 gct gct gag tac ttc ttc aaa agg ggt gtg caa gga aaa cag ttt cgt   384
Ala Ala Glu Tyr Phe Phe Lys Arg Gly Val Gln Gly Lys Gln Phe Arg
        115                 120                 125 tca act att ttg ctg ctg atg gcg aca gct ctg gat gta cga gtt cca   432
Ser Thr Ile Leu Leu Leu Met Ala Thr Ala Leu Asp Val Arg Val Pro
    130                 135                 140 gaa gca ttg att ggg gaa tca aca gat ata gtc aca tca gaa tta cgc   480
Glu Ala Leu Ile Gly Glu Ser Thr Asp Ile Val Thr Ser Glu Leu Arg
145                 150                 155                 160 gta agg caa cgg ggt att gct gaa atc act gaa atg ata cac gtc gca   528
Val Arg Gln Arg Gly Ile Ala Glu Ile Thr Glu Met Ile His Val Ala
                165                 170                 175 agt cta ctg cac gat gat gtc ttg gat gat gcc gat aca agg cgt ggt   576
Ser Leu Leu His Asp Asp Val Leu Asp Asp Ala Asp Thr Arg Arg Gly
            180                 185                 190 gtt ggt tcc tta aat gtt gta atg ggt aac aag atg tcg gta tta gca   624
Val Gly Ser Leu Asn Val Val Met Gly Asn Lys Met Ser Val Leu Ala
        195                 200                 205 gga gac ttc ttg ctc tcc cgg gct tgt ggg gct ctc gct gct tta aag   672
Gly Asp Phe Leu Leu Ser Arg Ala Cys Gly Ala Leu Ala Ala Leu Lys
```

```
aac aca gag gtt gta gca tta ctt gca act gct gta gaa cat ctt gtt      720
Asn Thr Glu Val Val Ala Leu Leu Ala Thr Ala Val Glu His Leu Val
225                 230                 235                 240 acc ggt gaa acc atg gag ata act agt tca acc gag cag cgt tat agt      768
Thr Gly Glu Thr Met Glu Ile Thr Ser Ser Thr Glu Gln Arg Tyr Ser
                245                 250                 255 atg gac tac tac atg cag aag aca tat tat aag aca gca tcg cta atc      816
Met Asp Tyr Tyr Met Gln Lys Thr Tyr Tyr Lys Thr Ala Ser Leu Ile
            260                 265                 270 tct aac agc tgc aaa gct gtt gcc gtt ctc act gga caa aca gca gaa      864
Ser Asn Ser Cys Lys Ala Val Ala Val Leu Thr Gly Gln Thr Ala Glu
        275                 280                 285 gtt gcc gtg tta gct ttt gag tat ggg agg aat ctg ggt tta gca ttc      912
Val Ala Val Leu Ala Phe Glu Tyr Gly Arg Asn Leu Gly Leu Ala Phe
    290                 295                 300 caa tta ata gac gac att ctt gat ttc acg ggc aca tct gcc tct ctc      960
Gln Leu Ile Asp Asp Ile Leu Asp Phe Thr Gly Thr Ser Ala Ser Leu
305                 310                 315                 320 gga aag gga tcg ttg tca gat att cgc cat gga gtc ata aca gcc cca     1008
Gly Lys Gly Ser Leu Ser Asp Ile Arg His Gly Val Ile Thr Ala Pro
                325                 330                 335 atc ctc ttt gcc atg gaa gag ttt cct caa cta cgc gaa gtt gtt gat     1056
Ile Leu Phe Ala Met Glu Glu Phe Pro Gln Leu Arg Glu Val Val Asp
            340                 345                 350 caa gtt gaa aaa gat cct agg aat gtt gac att gct tta gag tat ctt     1104
Gln Val Glu Lys Asp Pro Arg Asn Val Asp Ile Ala Leu Glu Tyr Leu
        355                 360                 365 ggg aag agc aag gga ata cag agg gca aga gaa tta gcc atg gaa cat     1152
Gly Lys Ser Lys Gly Ile Gln Arg Ala Arg Glu Leu Ala Met Glu His
    370                 375                 380 gcg aat cta gca gca gct gca atc ggg tct cta cct gaa aca gac aat     1200
Ala Asn Leu Ala Ala Ala Ala Ile Gly Ser Leu Pro Glu Thr Asp Asn
385                 390                 395                 400 gaa gat gtc aaa aga tcg agg cgg gca ctt att gac ttg acc cat aga     1248
Glu Asp Val Lys Arg Ser Arg Arg Ala Leu Ile Asp Leu Thr His Arg
                405                 410                 415 gtc atc acc aga aac aag tga                                         1269
Val Ile Thr Arg Asn Lys
            420
```

<210> SEQ ID NO 2
<211> LENGTH: 422
<212> TYPE: PRT
<213> ORGANISM: Arabidopsis thaliana

<400> SEQUENCE: 2

```
Met Leu Phe Thr Arg Ser Val Ala Arg Ile Ser Ser Lys Phe Leu Arg
1               5                   10                  15

Asn Arg Ser Phe Tyr Gly Ser Ser Gln Ser Leu Ala Ser His Arg Phe
            20                  25                  30

Ala Ile Ile Pro Asp Gln Gly His Ser Cys Ser Asp Ser Pro His Lys
        35                  40                  45

Gly Tyr Val Cys Arg Thr Thr Tyr Ser Leu Lys Ser Pro Val Phe Gly
    50                  55                  60

Gly Phe Ser His Gln Leu Tyr His Gln Ser Ser Leu Val Glu Glu
65                  70                  75                  80

Glu Leu Asp Pro Phe Ser Leu Val Ala Asp Glu Leu Ser Leu Leu Ser
                85                  90                  95
```

Asn Lys Leu Arg Glu Met Val Leu Ala Glu Val Pro Lys Leu Ala Ser
            100                 105                 110

Ala Ala Glu Tyr Phe Phe Lys Arg Gly Val Gln Gly Lys Gln Phe Arg
        115                 120                 125

Ser Thr Ile Leu Leu Leu Met Ala Thr Ala Leu Asp Val Arg Val Pro
    130                 135                 140

Glu Ala Leu Ile Gly Glu Ser Thr Asp Ile Val Thr Ser Glu Leu Arg
145                 150                 155                 160

Val Arg Gln Arg Gly Ile Ala Glu Ile Thr Glu Met Ile His Val Ala
                165                 170                 175

Ser Leu Leu His Asp Asp Val Leu Asp Asp Ala Asp Thr Arg Arg Gly
            180                 185                 190

Val Gly Ser Leu Asn Val Val Met Gly Asn Lys Met Ser Val Leu Ala
        195                 200                 205

Gly Asp Phe Leu Leu Ser Arg Ala Cys Gly Ala Leu Ala Ala Leu Lys
    210                 215                 220

Asn Thr Glu Val Val Ala Leu Leu Ala Thr Ala Val Glu His Leu Val
225                 230                 235                 240

Thr Gly Glu Thr Met Glu Ile Thr Ser Ser Thr Glu Gln Arg Tyr Ser
                245                 250                 255

Met Asp Tyr Tyr Met Gln Lys Thr Tyr Tyr Lys Thr Ala Ser Leu Ile
            260                 265                 270

Ser Asn Ser Cys Lys Ala Val Ala Val Leu Thr Gly Gln Thr Ala Glu
        275                 280                 285

Val Ala Val Leu Ala Phe Glu Tyr Gly Arg Asn Leu Gly Leu Ala Phe
    290                 295                 300

Gln Leu Ile Asp Asp Ile Leu Asp Phe Thr Gly Thr Ser Ala Ser Leu
305                 310                 315                 320

Gly Lys Gly Ser Leu Ser Asp Ile Arg His Gly Val Ile Thr Ala Pro
                325                 330                 335

Ile Leu Phe Ala Met Glu Glu Phe Pro Gln Leu Arg Glu Val Val Asp
            340                 345                 350

Gln Val Glu Lys Asp Pro Arg Asn Val Asp Ile Ala Leu Glu Tyr Leu
        355                 360                 365

Gly Lys Ser Lys Gly Ile Gln Arg Ala Arg Glu Leu Ala Met Glu His
    370                 375                 380

Ala Asn Leu Ala Ala Ala Ile Gly Ser Leu Pro Glu Thr Asp Asn
385                 390                 395                 400

Glu Asp Val Lys Arg Ser Arg Arg Ala Leu Ile Asp Leu Thr His Arg
                405                 410                 415

Val Ile Thr Arg Asn Lys
            420

<210> SEQ ID NO 3
<211> LENGTH: 912
<212> TYPE: DNA
<213> ORGANISM: Solanum lycopersicum
<220> FEATURE:
<221> NAME/KEY: CDS
<222> LOCATION: (1)..(912)
<223> OTHER INFORMATION:

<400> SEQUENCE: 3 atg agt tct ttg gtt ctt caa tgt tgg aaa tta tca tct cca tct ctg        48
Met Ser Ser Leu Val Leu Gln Cys Trp Lys Leu Ser Ser Pro Ser Leu
1               5                   10                  15

| | | | | | | | | | | | | | | | | |
|---|---|---|---|---|---|---|---|---|---|---|---|---|---|---|---|---|
| att | tta | caa | caa | aat | aca | tca | ata | tcc | atg | ggt | gca | ttc | aaa | ggt | att | 96 |
| Ile | Leu | Gln | Gln | Asn | Thr | Ser | Ile | Ser | Met | Gly | Ala | Phe | Lys | Gly | Ile | |
| | | | 20 | | | | | 25 | | | | | 30 | | | |
| cat | aaa | ctt | caa | atc | cca | aat | tcg | cct | ctg | aca | gtg | tct | gct | cgt | gga | 144 |
| His | Lys | Leu | Gln | Ile | Pro | Asn | Ser | Pro | Leu | Thr | Val | Ser | Ala | Arg | Gly | |
| | 35 | | | | | 40 | | | | | 45 | | | | | |
| ctc | aac | aag | att | tca | tgc | tca | ctc | aac | tta | caa | acc | gaa | aag | ctt | tgt | 192 |
| Leu | Asn | Lys | Ile | Ser | Cys | Ser | Leu | Asn | Leu | Gln | Thr | Glu | Lys | Leu | Cys | |
| 50 | | | | | 55 | | | | | 60 | | | | | | |
| tat | gag | gat | aat | gat | aat | gat | ctt | gat | gaa | gaa | ctt | atg | cct | aaa | cac | 240 |
| Tyr | Glu | Asp | Asn | Asp | Asn | Asp | Leu | Asp | Glu | Glu | Leu | Met | Pro | Lys | His | |
| 65 | | | | | 70 | | | | | 75 | | | | | 80 | |
| att | gct | ttg | ata | atg | gat | ggt | aat | agg | aga | tgg | gca | aag | gat | aag | ggt | 288 |
| Ile | Ala | Leu | Ile | Met | Asp | Gly | Asn | Arg | Arg | Trp | Ala | Lys | Asp | Lys | Gly | |
| | | | | 85 | | | | | 90 | | | | | 95 | | |
| tta | gaa | gta | tat | gaa | ggt | cac | aaa | cat | att | att | cca | aaa | tta | aaa | gag | 336 |
| Leu | Glu | Val | Tyr | Glu | Gly | His | Lys | His | Ile | Ile | Pro | Lys | Leu | Lys | Glu | |
| | | | | 100 | | | | | 105 | | | | | 110 | | |
| att | tgt | gac | att | tct | tct | aaa | ttg | gga | ata | caa | att | atc | act | gct | ttt | 384 |
| Ile | Cys | Asp | Ile | Ser | Ser | Lys | Leu | Gly | Ile | Gln | Ile | Ile | Thr | Ala | Phe | |
| | | 115 | | | | | 120 | | | | | 125 | | | | |
| gca | ttc | tct | act | gaa | aat | tgg | aaa | cga | tcc | aag | gag | gag | gtt | gat | ttc | 432 |
| Ala | Phe | Ser | Thr | Glu | Asn | Trp | Lys | Arg | Ser | Lys | Glu | Glu | Val | Asp | Phe | |
| | 130 | | | | | 135 | | | | | 140 | | | | | |
| ttg | ttg | caa | atg | ttc | gaa | gaa | atc | tat | gat | gag | ttt | tcg | agg | tct | gga | 480 |
| Leu | Leu | Gln | Met | Phe | Glu | Glu | Ile | Tyr | Asp | Glu | Phe | Ser | Arg | Ser | Gly | |
| 145 | | | | | 150 | | | | | 155 | | | | | 160 | |
| gta | aga | gtg | tct | att | ata | ggt | tgt | aaa | tcc | gac | ctc | cca | atg | aca | tta | 528 |
| Val | Arg | Val | Ser | Ile | Ile | Gly | Cys | Lys | Ser | Asp | Leu | Pro | Met | Thr | Leu | |
| | | | | 165 | | | | | 170 | | | | | 175 | | |
| caa | aaa | tgc | ata | gca | tta | aca | gaa | gag | act | aca | aag | ggc | aac | aaa | gga | 576 |
| Gln | Lys | Cys | Ile | Ala | Leu | Thr | Glu | Glu | Thr | Thr | Lys | Gly | Asn | Lys | Gly | |
| | | | 180 | | | | | 185 | | | | | 190 | | | |
| ctt | cac | ctt | gtg | att | gca | cta | aac | tat | ggt | gga | tat | tat | gac | ata | ttg | 624 |
| Leu | His | Leu | Val | Ile | Ala | Leu | Asn | Tyr | Gly | Gly | Tyr | Tyr | Asp | Ile | Leu | |
| | | 195 | | | | | 200 | | | | | 205 | | | | |
| caa | gca | aca | aaa | agc | att | gtt | aat | aaa | gca | atg | aat | ggt | tta | tta | gat | 672 |
| Gln | Ala | Thr | Lys | Ser | Ile | Val | Asn | Lys | Ala | Met | Asn | Gly | Leu | Leu | Asp | |
| | 210 | | | | | 215 | | | | | 220 | | | | | |
| gta | gaa | gat | atc | aac | aag | aat | tta | ttt | gat | caa | gaa | ctt | gaa | agc | aag | 720 |
| Val | Glu | Asp | Ile | Asn | Lys | Asn | Leu | Phe | Asp | Gln | Glu | Leu | Glu | Ser | Lys | |
| 225 | | | | | 230 | | | | | 235 | | | | | 240 | |
| tgt | cca | aat | cct | gat | tta | ctt | ata | agg | aca | gga | ggt | gaa | caa | aga | gtt | 768 |
| Cys | Pro | Asn | Pro | Asp | Leu | Leu | Ile | Arg | Thr | Gly | Gly | Glu | Gln | Arg | Val | |
| | | | | 245 | | | | | 250 | | | | | 255 | | |
| agt | aac | ttt | ttg | ttg | tgg | caa | ttg | gct | tac | act | gaa | ttt | tac | ttc | acc | 816 |
| Ser | Asn | Phe | Leu | Leu | Trp | Gln | Leu | Ala | Tyr | Thr | Glu | Phe | Tyr | Phe | Thr | |
| | | | 260 | | | | | 265 | | | | | 270 | | | |
| aac | aca | ttg | ttt | cct | gat | ttt | gga | gag | gaa | gat | ctt | aaa | gag | gca | ata | 864 |
| Asn | Thr | Leu | Phe | Pro | Asp | Phe | Gly | Glu | Glu | Asp | Leu | Lys | Glu | Ala | Ile | |
| | | 275 | | | | | 280 | | | | | 285 | | | | |
| atg | aac | ttt | caa | caa | agg | cat | aga | cgt | ttt | ggt | gga | cac | aca | tat | tga | 912 |
| Met | Asn | Phe | Gln | Gln | Arg | His | Arg | Arg | Phe | Gly | Gly | His | Thr | Tyr | | |
| | 290 | | | | | 295 | | | | | 300 | | | | | |

<210> SEQ ID NO 4
<211> LENGTH: 303
<212> TYPE: PRT
<213> ORGANISM: Solanum lycopersicum

<400> SEQUENCE: 4

```
Met Ser Ser Leu Val Leu Gln Cys Trp Lys Leu Ser Ser Pro Ser Leu
1               5                   10                  15

Ile Leu Gln Gln Asn Thr Ser Ile Ser Met Gly Ala Phe Lys Gly Ile
            20                  25                  30

His Lys Leu Gln Ile Pro Asn Ser Pro Leu Thr Val Ser Ala Arg Gly
        35                  40                  45

Leu Asn Lys Ile Ser Cys Ser Leu Asn Leu Gln Thr Glu Lys Leu Cys
    50                  55                  60

Tyr Glu Asp Asn Asp Asn Asp Leu Asp Glu Glu Leu Met Pro Lys His
65                  70                  75                  80

Ile Ala Leu Ile Met Asp Gly Asn Arg Arg Trp Ala Lys Asp Lys Gly
                85                  90                  95

Leu Glu Val Tyr Glu Gly His Lys His Ile Ile Pro Lys Leu Lys Glu
            100                 105                 110

Ile Cys Asp Ile Ser Ser Lys Leu Gly Ile Gln Ile Ile Thr Ala Phe
        115                 120                 125

Ala Phe Ser Thr Glu Asn Trp Lys Arg Ser Lys Glu Glu Val Asp Phe
    130                 135                 140

Leu Leu Gln Met Phe Glu Glu Ile Tyr Asp Glu Phe Ser Arg Ser Gly
145                 150                 155                 160

Val Arg Val Ser Ile Ile Gly Cys Lys Ser Asp Leu Pro Met Thr Leu
                165                 170                 175

Gln Lys Cys Ile Ala Leu Thr Glu Glu Thr Thr Lys Gly Asn Lys Gly
            180                 185                 190

Leu His Leu Val Ile Ala Leu Asn Tyr Gly Gly Tyr Tyr Asp Ile Leu
        195                 200                 205

Gln Ala Thr Lys Ser Ile Val Asn Lys Ala Met Asn Gly Leu Leu Asp
    210                 215                 220

Val Glu Asp Ile Asn Lys Asn Leu Phe Asp Gln Glu Leu Glu Ser Lys
225                 230                 235                 240

Cys Pro Asn Pro Asp Leu Leu Ile Arg Thr Gly Gly Glu Gln Arg Val
                245                 250                 255

Ser Asn Phe Leu Leu Trp Gln Leu Ala Tyr Thr Glu Phe Tyr Phe Thr
            260                 265                 270

Asn Thr Leu Phe Pro Asp Phe Gly Glu Glu Asp Leu Lys Glu Ala Ile
        275                 280                 285

Met Asn Phe Gln Gln Arg His Arg Arg Phe Gly Gly His Thr Tyr
    290                 295                 300
```

<210> SEQ ID NO 5
<211> LENGTH: 2337
<212> TYPE: DNA
<213> ORGANISM: Solanum lycopersicum
<220> FEATURE:
<221> NAME/KEY: CDS
<222> LOCATION: (1)..(2337)
<223> OTHER INFORMATION:

<400> SEQUENCE: 5

```
atg ata gtt ggc tat aga agc aca atc ata acc ctt tct cat cct aag      48
Met Ile Val Gly Tyr Arg Ser Thr Ile Ile Thr Leu Ser His Pro Lys
1               5                   10                  15 cta ggc aat ggg aaa aca att tca tcc aat gca att ttc cag aga tca      96
Leu Gly Asn Gly Lys Thr Ile Ser Ser Asn Ala Ile Phe Gln Arg Ser
            20                  25                  30
```

-continued

| | | | | | | | | | | | | | | | |
|---|---|---|---|---|---|---|---|---|---|---|---|---|---|---|---|
| tgt | aga | gta | aga | tgc | agc | cac | agt | acc | act | tca | tca | atg | aat | ggt | ttc | 144 |
| Cys | Arg | Val | Arg | Cys | Ser | His | Ser | Thr | Thr | Ser | Ser | Met | Asn | Gly | Phe | |
| | | 35 | | | | 40 | | | | | 45 | | | | | |

| gaa | gat | gca | agg | gat | aga | ata | agg | gaa | agt | ttt | ggg | aaa | tta | gag | tta | 192 |
| Glu | Asp | Ala | Arg | Asp | Arg | Ile | Arg | Glu | Ser | Phe | Gly | Lys | Leu | Glu | Leu | |
| 50 | | | | | 55 | | | | | 60 | | | | | | |

| tct | cct | tct | tcc | tat | gac | aca | gca | tgg | gta | gct | atg | gtc | cct | tca | aga | 240 |
| Ser | Pro | Ser | Ser | Tyr | Asp | Thr | Ala | Trp | Val | Ala | Met | Val | Pro | Ser | Arg | |
| 65 | | | | | 70 | | | | | 75 | | | | | 80 | |

| cat | tca | cta | aat | gag | cca | tgt | ttt | cca | caa | tgt | ttg | gat | tgg | att | att | 288 |
| His | Ser | Leu | Asn | Glu | Pro | Cys | Phe | Pro | Gln | Cys | Leu | Asp | Trp | Ile | Ile | |
| | | | | 85 | | | | | 90 | | | | | 95 | | |

| gaa | aat | caa | aga | gaa | gat | gga | tct | tgg | gga | cta | aac | cct | acc | cat | cca | 336 |
| Glu | Asn | Gln | Arg | Glu | Asp | Gly | Ser | Trp | Gly | Leu | Asn | Pro | Thr | His | Pro | |
| | | | 100 | | | | | 105 | | | | | 110 | | | |

| ttg | ctt | cta | aag | gac | tca | ctt | tct | tcc | act | ctt | gca | tgt | ttg | ctt | gca | 384 |
| Leu | Leu | Leu | Lys | Asp | Ser | Leu | Ser | Ser | Thr | Leu | Ala | Cys | Leu | Leu | Ala | |
| | | | | 115 | | | | | 120 | | | | | 125 | | |

| cta | acc | aaa | tgg | aga | gtt | gga | gat | gag | caa | atc | aaa | aga | ggt | ctt | ggc | 432 |
| Leu | Thr | Lys | Trp | Arg | Val | Gly | Asp | Glu | Gln | Ile | Lys | Arg | Gly | Leu | Gly | |
| | 130 | | | | | 135 | | | | | 140 | | | | | |

| ttc | att | gaa | acg | tat | ggt | tgg | gca | gta | gat | aac | aag | gat | caa | att | tca | 480 |
| Phe | Ile | Glu | Thr | Tyr | Gly | Trp | Ala | Val | Asp | Asn | Lys | Asp | Gln | Ile | Ser | |
| 145 | | | | | 150 | | | | | 155 | | | | | 160 | |

| cct | tta | gga | ttt | gaa | gtt | ata | ttt | tct | agt | atg | atc | aaa | tct | gca | gag | 528 |
| Pro | Leu | Gly | Phe | Glu | Val | Ile | Phe | Ser | Ser | Met | Ile | Lys | Ser | Ala | Glu | |
| | | | | 165 | | | | | 170 | | | | | 175 | | |

| aaa | tta | gat | tta | aat | ttg | cct | ttg | aat | ctt | cat | ctt | gta | aat | ttg | gtg | 576 |
| Lys | Leu | Asp | Leu | Asn | Leu | Pro | Leu | Asn | Leu | His | Leu | Val | Asn | Leu | Val | |
| | | | 180 | | | | | 185 | | | | | 190 | | | |

| aaa | tgc | aaa | aga | gat | tca | aca | att | aaa | agg | aat | gtt | gaa | tat | atg | ggt | 624 |
| Lys | Cys | Lys | Arg | Asp | Ser | Thr | Ile | Lys | Arg | Asn | Val | Glu | Tyr | Met | Gly | |
| | | | | 195 | | | | | 200 | | | | | 205 | | |

| gaa | gga | gtt | ggt | gaa | tta | tgt | gat | tgg | aag | gaa | atg | ata | aag | tta | cat | 672 |
| Glu | Gly | Val | Gly | Glu | Leu | Cys | Asp | Trp | Lys | Glu | Met | Ile | Lys | Leu | His | |
| | 210 | | | | | 215 | | | | | 220 | | | | | |

| caa | aga | caa | aat | ggt | tca | tta | ttt | gat | tca | cca | gcc | act | act | gca | gct | 720 |
| Gln | Arg | Gln | Asn | Gly | Ser | Leu | Phe | Asp | Ser | Pro | Ala | Thr | Thr | Ala | Ala | |
| 225 | | | | | 230 | | | | | 235 | | | | | 240 | |

| gcc | ttg | att | tat | cat | caa | cat | gat | caa | aaa | tgc | tat | caa | tat | ctt | aat | 768 |
| Ala | Leu | Ile | Tyr | His | Gln | His | Asp | Gln | Lys | Cys | Tyr | Gln | Tyr | Leu | Asn | |
| | | | | 245 | | | | | 250 | | | | | 255 | | |

| tca | atc | ttc | caa | caa | cac | aaa | aat | tgg | gtt | ccc | act | atg | tat | cca | aca | 816 |
| Ser | Ile | Phe | Gln | Gln | His | Lys | Asn | Trp | Val | Pro | Thr | Met | Tyr | Pro | Thr | |
| | | | | 260 | | | | | 265 | | | | | 270 | | |

| aag | gta | cat | tca | ttg | ctt | tgc | ttg | gtt | gat | aca | ctt | caa | aat | ctt | gga | 864 |
| Lys | Val | His | Ser | Leu | Leu | Cys | Leu | Val | Asp | Thr | Leu | Gln | Asn | Leu | Gly | |
| | | 275 | | | | | 280 | | | | | 285 | | | | |

| gta | cat | cgg | cat | ttt | aaa | tca | gaa | ata | aag | aaa | gct | cta | gat | gaa | ata | 912 |
| Val | His | Arg | His | Phe | Lys | Ser | Glu | Ile | Lys | Lys | Ala | Leu | Asp | Glu | Ile | |
| | 290 | | | | | 295 | | | | | 300 | | | | | |

| tac | agg | cta | tgg | caa | caa | aag | aat | gaa | caa | att | ttc | tca | aat | gtc | acc | 960 |
| Tyr | Arg | Leu | Trp | Gln | Gln | Lys | Asn | Glu | Gln | Ile | Phe | Ser | Asn | Val | Thr | |
| 305 | | | | | 310 | | | | | 315 | | | | | 320 | |

| cat | tgt | gct | atg | gct | ttt | cga | ctt | cta | agg | atg | agc | tac | tat | gat | gtc | 1008 |
| His | Cys | Ala | Met | Ala | Phe | Arg | Leu | Leu | Arg | Met | Ser | Tyr | Tyr | Asp | Val | |
| | | | | 325 | | | | | 330 | | | | | 335 | | |

| tcc | tca | gat | gaa | cta | gca | gaa | ttt | gtg | gat | gaa | gaa | cat | ttc | ttt | gca | 1056 |
| Ser | Ser | Asp | Glu | Leu | Ala | Glu | Phe | Val | Asp | Glu | Glu | His | Phe | Phe | Ala | |
| | | | 340 | | | | | 345 | | | | | 350 | | | |

```
aca aat ggg aaa tat aaa agt cat gtt gaa att ctt gaa ctc cac aaa    1104
Thr Asn Gly Lys Tyr Lys Ser His Val Glu Ile Leu Glu Leu His Lys
            355                 360                 365 gca tca caa ttg gct att gat cat gag aaa gat gac att ttg gat aaa    1152
Ala Ser Gln Leu Ala Ile Asp His Glu Lys Asp Asp Ile Leu Asp Lys
        370                 375                 380 ata aac aat tgg aca aga gct ttt atg gag caa aaa ctc tta aac aat    1200
Ile Asn Asn Trp Thr Arg Ala Phe Met Glu Gln Lys Leu Leu Asn Asn
385                 390                 395                 400 ggc ttc ata gat agg atg tca aag aaa gag gtg gaa ctt gct ttg agg    1248
Gly Phe Ile Asp Arg Met Ser Lys Lys Glu Val Glu Leu Ala Leu Arg
                405                 410                 415 aag ttt tat acc aca tct cat cta gca gaa aat aga aga tat ata aag    1296
Lys Phe Tyr Thr Thr Ser His Leu Ala Glu Asn Arg Arg Tyr Ile Lys
            420                 425                 430 tca tac gaa gag aac aat ttt aaa atc tta aaa gca gct tat agg tca    1344
Ser Tyr Glu Glu Asn Asn Phe Lys Ile Leu Lys Ala Ala Tyr Arg Ser
        435                 440                 445 ccc aac att aac aat aag gac ttg tta gca ttt tca ata cac gac ttt    1392
Pro Asn Ile Asn Asn Lys Asp Leu Leu Ala Phe Ser Ile His Asp Phe
450                 455                 460 gaa tta tgc caa gct caa cac cga gaa gaa ctt caa caa ctc aag agg    1440
Glu Leu Cys Gln Ala Gln His Arg Glu Glu Leu Gln Gln Leu Lys Arg
465                 470                 475                 480 tgg ttt gaa gat tat aga ttg gac caa ctc gga ctt gca gaa cga tat    1488
Trp Phe Glu Asp Tyr Arg Leu Asp Gln Leu Gly Leu Ala Glu Arg Tyr
                485                 490                 495 ata cat gct agt tac tta ttt ggt gtt act gtt atc ccc gag cct gaa    1536
Ile His Ala Ser Tyr Leu Phe Gly Val Thr Val Ile Pro Glu Pro Glu
            500                 505                 510 tta tcc gat gct cgc ctc atg tac gcg aaa tac gtc atg ctc ctg act    1584
Leu Ser Asp Ala Arg Leu Met Tyr Ala Lys Tyr Val Met Leu Leu Thr
        515                 520                 525 att gtc gat gat cat ttc gag agt ttt gca tct aaa gat gaa tgt ttc    1632
Ile Val Asp Asp His Phe Glu Ser Phe Ala Ser Lys Asp Glu Cys Phe
530                 535                 540 aac atc att gaa tta gta gaa agg tgg gat gac tat gca agt gta ggt    1680
Asn Ile Ile Glu Leu Val Glu Arg Trp Asp Asp Tyr Ala Ser Val Gly
545                 550                 555                 560 tat aaa tct gag aag gtt aaa gtt ttt ttt tct gtt ttc tat aaa tca    1728
Tyr Lys Ser Glu Lys Val Lys Val Phe Phe Ser Val Phe Tyr Lys Ser
                565                 570                 575 ata gag gag ctt gca aca att gct gaa att aaa caa gga cga tcc gtc    1776
Ile Glu Glu Leu Ala Thr Ile Ala Glu Ile Lys Gln Gly Arg Ser Val
            580                 585                 590 aaa aat cac ctt att aat ttg tgg ctt gaa ttg atg aag ttg atg ttg    1824
Lys Asn His Leu Ile Asn Leu Trp Leu Glu Leu Met Lys Leu Met Leu
        595                 600                 605 atg gag cga gta gag tgg tgt tct ggc aag aca ata cca agc ata gaa    1872
Met Glu Arg Val Glu Trp Cys Ser Gly Lys Thr Ile Pro Ser Ile Glu
610                 615                 620 gag tac ttg tat gtt aca tct ata aca ttt tgt gca aaa ttg att cct    1920
Glu Tyr Leu Tyr Val Thr Ser Ile Thr Phe Cys Ala Lys Leu Ile Pro
625                 630                 635                 640 ctc tca aca caa tat ttt ctt gga ata aaa ata tcc aaa gat cta cta    1968
Leu Ser Thr Gln Tyr Phe Leu Gly Ile Lys Ile Ser Lys Asp Leu Leu
                645                 650                 655 gaa agt gat gaa ata tgt ggc cta tgg aat tgt agc ggt aga gtg atg    2016
Glu Ser Asp Glu Ile Cys Gly Leu Trp Asn Cys Ser Gly Arg Val Met
```

```
                     660                 665                 670
cga atc ctt aat gat tta caa gat tcc aag aga gaa caa aag gag gtc      2064
Arg Ile Leu Asn Asp Leu Gln Asp Ser Lys Arg Glu Gln Lys Glu Val
            675                 680                 685 tca ata aat tta gtc aca tta cta atg aaa agt atg tct gag gaa gaa      2112
Ser Ile Asn Leu Val Thr Leu Leu Met Lys Ser Met Ser Glu Glu Glu
690                 695                 700 gct ata atg aag ata aag gaa atc ttg gaa atg aat aga aga gag tta      2160
Ala Ile Met Lys Ile Lys Glu Ile Leu Glu Met Asn Arg Arg Glu Leu
705                 710                 715                 720 ttg aaa atg gtt tta gtt caa aaa aag gga agc caa ttg cct caa tta      2208
Leu Lys Met Val Leu Val Gln Lys Lys Gly Ser Gln Leu Pro Gln Leu
            725                 730                 735 tgc aaa gat ata ttt tgg agg aca agc aaa tgg gct cat ttc act tat      2256
Cys Lys Asp Ile Phe Trp Arg Thr Ser Lys Trp Ala His Phe Thr Tyr
            740                 745                 750 tca caa act gat gga tat aga att gca gag gaa atg aag aat cac att      2304
Ser Gln Thr Asp Gly Tyr Arg Ile Ala Glu Glu Met Lys Asn His Ile
            755                 760                 765 gat gaa gtc ttt tac aaa cca ctc aat cat taa                          2337
Asp Glu Val Phe Tyr Lys Pro Leu Asn His
    770                 775

<210> SEQ ID NO 6
<211> LENGTH: 778
<212> TYPE: PRT
<213> ORGANISM: Solanum lycopersicum

<400> SEQUENCE: 6

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Gln Arg Ser
            20                  25                  30

Cys Arg Val Arg Cys Ser His Ser Thr Thr Ser Ser Met Asn Gly Phe
        35                  40                  45

Glu Asp Ala Arg Asp Arg Ile Arg Glu Ser Phe Gly Lys Leu Glu Leu
    50                  55                  60

Ser Pro Ser Ser Tyr Asp Thr Ala Trp Val Ala Met Val Pro Ser Arg
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Thr His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Tyr Gly Trp Ala Val Asp Asn Lys Asp Gln Ile Ser
145                 150                 155                 160

Pro Leu Gly Phe Glu Val Ile Phe Ser Met Ile Lys Ser Ala Glu
                165                 170                 175

Lys Leu Asp Leu Asn Leu Pro Leu Asn Leu His Leu Val Asn Leu Val
            180                 185                 190

Lys Cys Lys Arg Asp Ser Thr Ile Lys Arg Asn Val Glu Tyr Met Gly
        195                 200                 205

Glu Gly Val Gly Glu Leu Cys Asp Trp Lys Glu Met Ile Lys Leu His
    210                 215                 220
```

-continued

```
Gln Arg Gln Asn Gly Ser Leu Phe Asp Ser Pro Ala Thr Thr Ala Ala
225                 230                 235                 240

Ala Leu Ile Tyr His Gln His Asp Gln Lys Cys Tyr Gln Tyr Leu Asn
                245                 250                 255

Ser Ile Phe Gln Gln His Lys Asn Trp Val Pro Thr Met Tyr Pro Thr
            260                 265                 270

Lys Val His Ser Leu Leu Cys Leu Val Asp Thr Leu Gln Asn Leu Gly
        275                 280                 285

Val His Arg His Phe Lys Ser Glu Ile Lys Lys Ala Leu Asp Glu Ile
    290                 295                 300

Tyr Arg Leu Trp Gln Gln Lys Asn Glu Gln Ile Phe Ser Asn Val Thr
305                 310                 315                 320

His Cys Ala Met Ala Phe Arg Leu Leu Arg Met Ser Tyr Tyr Asp Val
                325                 330                 335

Ser Ser Asp Glu Leu Ala Glu Phe Val Asp Glu His Phe Phe Ala
            340                 345                 350

Thr Asn Gly Lys Tyr Lys Ser His Val Glu Ile Leu Glu Leu His Lys
        355                 360                 365

Ala Ser Gln Leu Ala Ile Asp His Glu Lys Asp Ile Leu Asp Lys
370                 375                 380

Ile Asn Asn Trp Thr Arg Ala Phe Met Glu Gln Lys Leu Leu Asn Asn
385                 390                 395                 400

Gly Phe Ile Asp Arg Met Ser Lys Lys Glu Val Glu Leu Ala Leu Arg
                405                 410                 415

Lys Phe Tyr Thr Thr Ser His Leu Ala Glu Asn Arg Arg Tyr Ile Lys
            420                 425                 430

Ser Tyr Glu Glu Asn Asn Phe Lys Ile Leu Lys Ala Ala Tyr Arg Ser
        435                 440                 445

Pro Asn Ile Asn Asn Lys Asp Leu Leu Ala Phe Ser Ile His Asp Phe
    450                 455                 460

Glu Leu Cys Gln Ala Gln His Arg Glu Glu Leu Gln Gln Leu Lys Arg
465                 470                 475                 480

Trp Phe Glu Asp Tyr Arg Leu Asp Gln Leu Gly Leu Ala Glu Arg Tyr
                485                 490                 495

Ile His Ala Ser Tyr Leu Phe Gly Val Thr Val Ile Pro Glu Pro Glu
            500                 505                 510

Leu Ser Asp Ala Arg Leu Met Tyr Ala Lys Tyr Val Met Leu Leu Thr
        515                 520                 525

Ile Val Asp Asp His Phe Glu Ser Phe Ala Ser Lys Asp Glu Cys Phe
    530                 535                 540

Asn Ile Ile Glu Leu Val Glu Arg Trp Asp Asp Tyr Ala Ser Val Gly
545                 550                 555                 560

Tyr Lys Ser Glu Lys Val Lys Val Phe Phe Ser Val Phe Tyr Lys Ser
                565                 570                 575

Ile Glu Glu Leu Ala Thr Ile Ala Glu Ile Lys Gln Gly Arg Ser Val
            580                 585                 590

Lys Asn His Leu Ile Asn Leu Trp Leu Glu Leu Met Lys Leu Met Leu
        595                 600                 605

Met Glu Arg Val Glu Trp Cys Ser Gly Lys Thr Ile Pro Ser Ile Glu
    610                 615                 620

Glu Tyr Leu Tyr Val Thr Ser Ile Thr Phe Cys Ala Lys Leu Ile Pro
625                 630                 635                 640
```

```
                                    -continued

Leu Ser Thr Gln Tyr Phe Leu Gly Ile Lys Ile Ser Lys Asp Leu Leu
            645                 650                 655

Glu Ser Asp Glu Ile Cys Gly Leu Trp Asn Cys Ser Gly Arg Val Met
        660                 665                 670

Arg Ile Leu Asn Asp Leu Gln Asp Ser Lys Arg Glu Gln Lys Glu Val
            675                 680                 685

Ser Ile Asn Leu Val Thr Leu Leu Met Lys Ser Met Ser Glu Glu Glu
        690                 695                 700

Ala Ile Met Lys Ile Lys Glu Ile Leu Glu Met Asn Arg Arg Glu Leu
705                 710                 715                 720

Leu Lys Met Val Leu Val Gln Lys Lys Gly Ser Gln Leu Pro Gln Leu
                725                 730                 735

Cys Lys Asp Ile Phe Trp Arg Thr Ser Lys Trp Ala His Phe Thr Tyr
            740                 745                 750

Ser Gln Thr Asp Gly Tyr Arg Ile Ala Glu Glu Met Lys Asn His Ile
        755                 760                 765

Asp Glu Val Phe Tyr Lys Pro Leu Asn His
            770                 775

<210> SEQ ID NO 7
<211> LENGTH: 1746
<212> TYPE: DNA
<213> ORGANISM: Lavandula angustifolia
<220> FEATURE:
<221> NAME/KEY: CDS
<222> LOCATION: (1)..(1746)
<223> OTHER INFORMATION:

<400> SEQUENCE: 7 atg tct acc att att gcg ata caa gtg ttg ctt cct att cca act act     48
Met Ser Thr Ile Ile Ala Ile Gln Val Leu Leu Pro Ile Pro Thr Thr
1               5                   10                  15 aaa aca tac cct agt cat gac ttg gag aag tcc tct tcg cgg tgt cgc     96
Lys Thr Tyr Pro Ser His Asp Leu Glu Lys Ser Ser Ser Arg Cys Arg
            20                  25                  30 tcc tcc tcc act cct cgc cct aga ctg tgt tgc tcg ttg cag gtg agt    144
Ser Ser Ser Thr Pro Arg Pro Arg Leu Cys Cys Ser Leu Gln Val Ser
        35                  40                  45 gat ccg atc cca acg ggc cgg cga tcc gga ggc tac ccg ccc gcc cta    192
Asp Pro Ile Pro Thr Gly Arg Arg Ser Gly Gly Tyr Pro Pro Ala Leu
    50                  55                  60 tgg gat ttc gac act att caa tcg ctc aac acc gag tat aag gga gag    240
Trp Asp Phe Asp Thr Ile Gln Ser Leu Asn Thr Glu Tyr Lys Gly Glu
65                  70                  75                  80 agg cac atg aga agg gaa gaa gac cta att ggg caa gtt aga gag atg    288
Arg His Met Arg Arg Glu Glu Asp Leu Ile Gly Gln Val Arg Glu Met
                85                  90                  95 ctg gtg cat gaa gta gag gat ccc act cca cag ctg gag ttc att gat    336
Leu Val His Glu Val Glu Asp Pro Thr Pro Gln Leu Glu Phe Ile Asp
            100                 105                 110 gat ttg cat aag ctt ggc ata tct tgc cat ttt gag aat gaa atc ctc    384
Asp Leu His Lys Leu Gly Ile Ser Cys His Phe Glu Asn Glu Ile Leu
        115                 120                 125 caa atc ttg aaa tcc ata tat ctt aat caa aac tac aaa agg gat ttg    432
Gln Ile Leu Lys Ser Ile Tyr Leu Asn Gln Asn Tyr Lys Arg Asp Leu
    130                 135                 140 tac tca aca tct cta gca ttc aga ctc ctc aga caa tat ggc ttc atc    480
Tyr Ser Thr Ser Leu Ala Phe Arg Leu Leu Arg Gln Tyr Gly Phe Ile
145                 150                 155                 160
```

-continued

| | | |
|---|---|---|
| ctt cca caa gaa gta ttt gat tgt ttc aag aat gag gag ggt acg gat<br>Leu Pro Gln Glu Val Phe Asp Cys Phe Lys Asn Glu Glu Gly Thr Asp<br>165                170                175 | 528 |
| ttc aag cca agc ttc ggc cgt gat atc aaa ggc ttg tta caa ttg tat<br>Phe Lys Pro Ser Phe Gly Arg Asp Ile Lys Gly Leu Leu Gln Leu Tyr<br>            180                185                190 | 576 |
| gaa gct tct ttc cta tca aga aaa gga gaa gaa act tta caa cta gca<br>Glu Ala Ser Phe Leu Ser Arg Lys Gly Glu Glu Thr Leu Gln Leu Ala<br>195                200                205 | 624 |
| aga gag ttt gca aca aag att ctg caa aaa gaa gtt gat gag aga gag<br>Arg Glu Phe Ala Thr Lys Ile Leu Gln Lys Glu Val Asp Glu Arg Glu<br>210                215                220 | 672 |
| ttt gca acc aag atg gag ttc cct tct cat tgg acg gtt caa atg ccg<br>Phe Ala Thr Lys Met Glu Phe Pro Ser His Trp Thr Val Gln Met Pro<br>225                230                235                240 | 720 |
| aat gca aga cct ttc atc gat gct tac cgt agg agg ccg gat atg aat<br>Asn Ala Arg Pro Phe Ile Asp Ala Tyr Arg Arg Arg Pro Asp Met Asn<br>                245                250                255 | 768 |
| cca gtt gtg ctc gag cta gcc ata ctt gat aca aat ata gtt caa gca<br>Pro Val Val Leu Glu Leu Ala Ile Leu Asp Thr Asn Ile Val Gln Ala<br>            260                265                270 | 816 |
| caa ttt caa gaa gaa ctc aaa gag acc tca agg tgg tgg gag agt aca<br>Gln Phe Gln Glu Glu Leu Lys Glu Thr Ser Arg Trp Trp Glu Ser Thr<br>275                280                285 | 864 |
| ggc att gtc caa gag ctt cca ttt gtg agg gat agg att gtg gaa ggc<br>Gly Ile Val Gln Glu Leu Pro Phe Val Arg Asp Arg Ile Val Glu Gly<br>290                295                300 | 912 |
| tac ttt tgg acg att gga gtg act cag aga cgc gag cat gga tac gaa<br>Tyr Phe Trp Thr Ile Gly Val Thr Gln Arg Arg Glu His Gly Tyr Glu<br>305                310                315                320 | 960 |
| aga atc atg acc gca aag gtt att gcc tta gta aca tgt tta gac gac<br>Arg Ile Met Thr Ala Lys Val Ile Ala Leu Val Thr Cys Leu Asp Asp<br>                325                330                335 | 1008 |
| ata tac gat gtt tat ggc acg ata gaa gag ctt caa ctt ttc aca agc<br>Ile Tyr Asp Val Tyr Gly Thr Ile Glu Glu Leu Gln Leu Phe Thr Ser<br>            340                345                350 | 1056 |
| aca atc caa aga tgg gat ttg gaa tca atg aag caa ctc cct acc tac<br>Thr Ile Gln Arg Trp Asp Leu Glu Ser Met Lys Gln Leu Pro Thr Tyr<br>355                360                365 | 1104 |
| atg caa gta agc ttt ctt gca cta cac aac ttt gta acc gag gtg gct<br>Met Gln Val Ser Phe Leu Ala Leu His Asn Phe Val Thr Glu Val Ala<br>370                375                380 | 1152 |
| tac gat act ctc aag aaa aag ggc tac aac tcc aca cca tat tta aga<br>Tyr Asp Thr Leu Lys Lys Lys Gly Tyr Asn Ser Thr Pro Tyr Leu Arg<br>385                390                395                400 | 1200 |
| aaa acg tgg gtg gat ctt gtt gaa tca tat atc aaa gag gca act tgg<br>Lys Thr Trp Val Asp Leu Val Glu Ser Tyr Ile Lys Glu Ala Thr Trp<br>            405                410                415 | 1248 |
| tac tac aac ggt tat aaa cct agt atg caa gaa tac ctt aac aat gca<br>Tyr Tyr Asn Gly Tyr Lys Pro Ser Met Gln Glu Tyr Leu Asn Asn Ala<br>            420                425                430 | 1296 |
| tgg ata tca gtc gga agt atg gct ata ctc aac cac ctc ttc ttc cgg<br>Trp Ile Ser Val Gly Ser Met Ala Ile Leu Asn His Leu Phe Phe Arg<br>            435                440                445 | 1344 |
| ttc aca aac gag aga atg cat aaa tac cgc gat atg aac cgt gtc tcg<br>Phe Thr Asn Glu Arg Met His Lys Tyr Arg Asp Met Asn Arg Val Ser<br>450                455                460 | 1392 |
| tcc aac att gtg agg ctt gct gat gat atg gga aca tca ttg gct gag<br>Ser Asn Ile Val Arg Leu Ala Asp Asp Met Gly Thr Ser Leu Ala Glu<br>465                470                475                480 | 1440 |

-continued

```
gtg gag aga ggg gac gtg ccg aaa gca att caa tgc tac atg aat gag     1488
Val Glu Arg Gly Asp Val Pro Lys Ala Ile Gln Cys Tyr Met Asn Glu
                485                 490                 495 acg aat gct tct gaa gaa gaa gca aga gaa tat gta aga aga gtc ata     1536
Thr Asn Ala Ser Glu Glu Glu Ala Arg Glu Tyr Val Arg Arg Val Ile
        500                 505                 510 cag gaa gaa tgg gaa aag ttg aac aca gaa ttg atg cgg gat gat gat     1584
Gln Glu Glu Trp Glu Lys Leu Asn Thr Glu Leu Met Arg Asp Asp Asp
            515                 520                 525 gat gat gat gat ttt aca cta tcc aaa tat tac tgt gag gtg gtt gct     1632
Asp Asp Asp Asp Phe Thr Leu Ser Lys Tyr Tyr Cys Glu Val Val Ala
530                 535                 540 aat ctt aca aga atg gca cag ttt ata tac caa gat gga tcg gat ggc     1680
Asn Leu Thr Arg Met Ala Gln Phe Ile Tyr Gln Asp Gly Ser Asp Gly
545                 550                 555                 560 ttc ggc atg aaa gat tcc aag gtt aat aga ctg cta aaa gag acg ttg     1728
Phe Gly Met Lys Asp Ser Lys Val Asn Arg Leu Leu Lys Glu Thr Leu
                565                 570                 575 atc gag cgc tac gaa taa                                             1746
Ile Glu Arg Tyr Glu
            580
```

<210> SEQ ID NO 8
<211> LENGTH: 581
<212> TYPE: PRT
<213> ORGANISM: Lavandula angustifolia

<400> SEQUENCE: 8

```
Met Ser Thr Ile Ile Ala Ile Gln Val Leu Leu Pro Ile Pro Thr Thr
1               5                   10                  15

Lys Thr Tyr Pro Ser His Asp Leu Glu Lys Ser Ser Ser Arg Cys Arg
            20                  25                  30

Ser Ser Ser Thr Pro Arg Pro Arg Leu Cys Cys Ser Leu Gln Val Ser
        35                  40                  45

Asp Pro Ile Pro Thr Gly Arg Arg Ser Gly Gly Tyr Pro Pro Ala Leu
    50                  55                  60

Trp Asp Phe Asp Thr Ile Gln Ser Leu Asn Thr Glu Tyr Lys Gly Glu
65                  70                  75                  80

Arg His Met Arg Arg Glu Glu Asp Leu Ile Gly Gln Val Arg Glu Met
                85                  90                  95

Leu Val His Glu Val Glu Asp Pro Thr Pro Gln Leu Glu Phe Ile Asp
            100                 105                 110

Asp Leu His Lys Leu Gly Ile Ser Cys His Phe Glu Asn Glu Ile Leu
        115                 120                 125

Gln Ile Leu Lys Ser Ile Tyr Leu Asn Gln Asn Tyr Lys Arg Asp Leu
    130                 135                 140

Tyr Ser Thr Ser Leu Ala Phe Arg Leu Leu Arg Gln Tyr Gly Phe Ile
145                 150                 155                 160

Leu Pro Gln Glu Val Phe Asp Cys Phe Lys Asn Glu Glu Gly Thr Asp
                165                 170                 175

Phe Lys Pro Ser Phe Gly Arg Asp Ile Lys Gly Leu Leu Gln Leu Tyr
            180                 185                 190

Glu Ala Ser Phe Leu Ser Arg Lys Gly Glu Glu Thr Leu Gln Leu Ala
        195                 200                 205

Arg Glu Phe Ala Thr Lys Ile Leu Gln Lys Glu Val Asp Glu Arg Glu
    210                 215                 220
```

```
Phe Ala Thr Lys Met Glu Phe Pro Ser His Trp Thr Val Gln Met Pro
225                 230                 235                 240

Asn Ala Arg Pro Phe Ile Asp Ala Tyr Arg Arg Pro Asp Met Asn
        245                 250                 255

Pro Val Val Leu Glu Leu Ala Ile Leu Asp Thr Asn Ile Val Gln Ala
            260                 265                 270

Gln Phe Gln Glu Glu Leu Lys Glu Thr Ser Arg Trp Trp Glu Ser Thr
        275                 280                 285

Gly Ile Val Gln Glu Leu Pro Phe Val Arg Asp Arg Ile Val Glu Gly
            290                 295                 300

Tyr Phe Trp Thr Ile Gly Val Thr Gln Arg Arg Glu His Gly Tyr Glu
305                 310                 315                 320

Arg Ile Met Thr Ala Lys Val Ile Ala Leu Val Thr Cys Leu Asp Asp
                325                 330                 335

Ile Tyr Asp Val Tyr Gly Thr Ile Glu Glu Leu Gln Leu Phe Thr Ser
                340                 345                 350

Thr Ile Gln Arg Trp Asp Leu Glu Ser Met Lys Gln Leu Pro Thr Tyr
        355                 360                 365

Met Gln Val Ser Phe Leu Ala Leu His Asn Phe Val Thr Glu Val Ala
370                 375                 380

Tyr Asp Thr Leu Lys Lys Lys Gly Tyr Asn Ser Thr Pro Tyr Leu Arg
385                 390                 395                 400

Lys Thr Trp Val Asp Leu Val Glu Ser Tyr Ile Lys Glu Ala Thr Trp
                405                 410                 415

Tyr Tyr Asn Gly Tyr Lys Pro Ser Met Gln Glu Tyr Leu Asn Asn Ala
            420                 425                 430

Trp Ile Ser Val Gly Ser Met Ala Ile Leu Asn His Leu Phe Phe Arg
        435                 440                 445

Phe Thr Asn Glu Arg Met His Lys Tyr Arg Asp Met Asn Arg Val Ser
450                 455                 460

Ser Asn Ile Val Arg Leu Ala Asp Asp Met Gly Thr Ser Leu Ala Glu
465                 470                 475                 480

Val Glu Arg Gly Asp Val Pro Lys Ala Ile Gln Cys Tyr Met Asn Glu
                485                 490                 495

Thr Asn Ala Ser Glu Glu Ala Arg Glu Tyr Val Arg Arg Val Ile
            500                 505                 510

Gln Glu Glu Trp Glu Lys Leu Asn Thr Glu Leu Met Arg Asp Asp Asp
        515                 520                 525

Asp Asp Asp Asp Phe Thr Leu Ser Lys Tyr Tyr Cys Glu Val Val Ala
530                 535                 540

Asn Leu Thr Arg Met Ala Gln Phe Ile Tyr Gln Asp Gly Ser Asp Gly
545                 550                 555                 560

Phe Gly Met Lys Asp Ser Lys Val Asn Arg Leu Leu Lys Glu Thr Leu
                565                 570                 575

Ile Glu Arg Tyr Glu
            580

<210> SEQ ID NO 9
<211> LENGTH: 32
<212> TYPE: DNA
<213> ORGANISM: Artificial
<220> FEATURE:
<223> OTHER INFORMATION: Designed oligonucleotide primer for PCR

<400> SEQUENCE: 9
```
gcgggccata tgagttcttt ggttcttcaa tg        32

<210> SEQ ID NO 10
<211> LENGTH: 35
<212> TYPE: DNA
<213> ORGANISM: Artificial
<220> FEATURE:
<223> OTHER INFORMATION: Designed oligonucleotide primer for PCR

<400> SEQUENCE: 10
gcccgcgaat tctcaatatg tgtgtccacc aaaac        35

<210> SEQ ID NO 11
<211> LENGTH: 31
<212> TYPE: DNA
<213> ORGANISM: Artificial
<220> FEATURE:
<223> OTHER INFORMATION: Designed oligonucleotide primer for PCR

<400> SEQUENCE: 11
gcgggcccat ggtagttggc tatagaagca c        31

<210> SEQ ID NO 12
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 12
ggccgcggat ccttaatgat tgagtggttt gtaaaag        37

<210> SEQ ID NO 13
<211> LENGTH: 32
<212> TYPE: DNA
<213> ORGANISM: Artificial
<220> FEATURE:
<223> OTHER INFORMATION: Designed oligonucleotide primer for PCR

<400> SEQUENCE: 13
gcgggccata tgctattcac caggagtgtt gc        32

<210> SEQ ID NO 14
<211> LENGTH: 33
<212> TYPE: DNA
<213> ORGANISM: Artificial
<220> FEATURE:
<223> OTHER INFORMATION: Designed oligonucleotide primer for PCR

<400> SEQUENCE: 14
gcccgcgaat tctcacttgt ttctggtgat gac        33

<210> SEQ ID NO 15
<211> LENGTH: 31
<212> TYPE: DNA
<213> ORGANISM: Artificial
<220> FEATURE:
<223> OTHER INFORMATION: Designed oligonucleotide primer for PCR

<400> SEQUENCE: 15
gcgggccata tgtctaccat tattgcgata c        31

<210> SEQ ID NO 16
<211> LENGTH: 34
<212> TYPE: DNA
<213> ORGANISM: Artificial

```
<220> FEATURE:
<223> OTHER INFORMATION: Designed oligonucleotide primer for PCR

<400> SEQUENCE: 16
gcccgcgaat tcttattcgt agcgctcgat caac                          34

<210> SEQ ID NO 17
<211> LENGTH: 38
<212> TYPE: DNA
<213> ORGANISM: Artificial
<220> FEATURE:
<223> OTHER INFORMATION: Designed oligonucleotide primer for PCR

<400> SEQUENCE: 17
gcgggcggat ccaccatggg ttctttggtt cttcaatg                      38

<210> SEQ ID NO 18
<211> LENGTH: 35
<212> TYPE: DNA
<213> ORGANISM: Artificial
<220> FEATURE:
<223> OTHER INFORMATION: Designed oligonucleotide primer for PCR

<400> SEQUENCE: 18
gcccgcggat cctcaatatg tgtgtccacc aaaac                         35

<210> SEQ ID NO 19
<211> LENGTH: 38
<212> TYPE: DNA
<213> ORGANISM: Artificial
<220> FEATURE:
<223> OTHER INFORMATION: Designed oligonucleotide primer for PCR

<400> SEQUENCE: 19
gcgggcggat ccaccatggt agttggctat agaagcac                      38

<210> SEQ ID NO 20
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 20
gcccgcggat ccttaatgat tgagtggttt gtaaaag                       37

<210> SEQ ID NO 21
<211> LENGTH: 38
<212> TYPE: DNA
<213> ORGANISM: Artificial
<220> FEATURE:
<223> OTHER INFORMATION: Designed oligonucleotide primer for PCR

<400> SEQUENCE: 21
gcgggcggat ccaccatggt attcacgagg agtgttgc                      38

<210> SEQ ID NO 22
<211> LENGTH: 33
<212> TYPE: DNA
<213> ORGANISM: Artificial
<220> FEATURE:
<223> OTHER INFORMATION: Designed oligonucleotide primer for PCR
```

<400> SEQUENCE: 22
gcccgcggat cctcacttgt ttctggtgat gac        33

<210> SEQ ID NO 23
<211> LENGTH: 37
<212> TYPE: DNA
<213> ORGANISM: Artificial
<220> FEATURE:
<223> OTHER INFORMATION: Designed oligonucleotide primer for PCR

<400> SEQUENCE: 23
gcgggcgaat tcaccatggc taccattatt gcgatac        37

<210> SEQ ID NO 24
<211> LENGTH: 34
<212> TYPE: DNA
<213> ORGANISM: Artificial
<220> FEATURE:
<223> OTHER INFORMATION: Designed oligonucleotide primer for PCR

<400> SEQUENCE: 24
gcccgcgaat tcttattcgt agcgctcgat caac        34

<210> SEQ ID NO 25
<211> LENGTH: 32
<212> TYPE: DNA
<213> ORGANISM: Artificial
<220> FEATURE:
<223> OTHER INFORMATION: Designed oligonucleotide primer for PCR

<400> SEQUENCE: 25
aggaggcata tgagttcttt ggttcttcaa tg        32

<210> SEQ ID NO 26
<211> LENGTH: 35
<212> TYPE: DNA
<213> ORGANISM: Artificial
<220> FEATURE:
<223> OTHER INFORMATION: Designed oligonucleotide primer for PCR

<400> SEQUENCE: 26
tcctccggat cctcaatatg tgtgtccacc aaaac        35

<210> SEQ ID NO 27
<211> LENGTH: 25
<212> TYPE: DNA
<213> ORGANISM: Artificial
<220> FEATURE:
<223> OTHER INFORMATION: Designed oligonucleotide primer for PCR

<400> SEQUENCE: 27
accatggctc ttccgacctc ggtgg        25

<210> SEQ ID NO 28
<211> LENGTH: 25
<212> TYPE: DNA
<213> ORGANISM: Artificial
<220> FEATURE:
<223> OTHER INFORMATION: Designed oligonucleotide primer for PCR

<400> SEQUENCE: 28
tgaattctca gcacgctcgg tagag                                                25

<210> SEQ ID NO 29
<211> LENGTH: 6441
<212> TYPE: DNA
<213> ORGANISM: Streptomyces griseolosporeus

<400> SEQUENCE: 29

```
gttgactctt ccgacctcgg tggaggaggg atcgaaggcc caccgggctc gcgccgtcgg      60
caccggtcgc gctcatgcca aggccattct gctgggagag cacgcggtcg tgtacggaac     120
cccggcgctc gcgatgccca ttccccaact cgcggtcacg gcaagcgccg gctggtccgg     180
ccgatccgcc gagagccggg gcggtccgac cttcaccatg accgggtcgg cttcccgcgc     240
ggtcacggca caggccttgg acggtctgcg acgtctgacc gcctcggtca aggcgcacac     300
gggagtgacc gacggacaac acctcgacgt cagcctcgac ggggcgattc cgcccggccg     360
cgggctcggc tccagcgccg cgaacgcacg agcgatcatc ctcgccctgg ccgacctctt     420
cggccgggag ctgaccgagg cgaggtgtt cgacctggtg caggaggccg agaacctgac     480
gcacggccgg gccagcggcg tcgacgccgt gaccgtcggc gccaccgccc cgctcctctt     540
ccgggcgggc acggcacagg cgctggacat cggctgcgac gcactgttcg tcgtcgcgga     600
cagcggaacc gcagggagca ccaaggaggc gatcgagctg cttcgcgccg gattccgggc     660
cggggccgga aaggaggaac ggttcatgca ccgtgccgcg cacctcgtcg acgatgccag     720
ggcctcccctc gccgagggcg aacccgaggc gttcggatcg tgcctgaccg agtatcacgg     780
cctgctgcgc ggggcgggtc tgagcaccga ccggatcgat gcactggtgg atgccgcgct     840
gcaggccgac agcctgggcg ccaagatcac cggtggcggt ctgggcggtt gtgttctcgc     900
gatgtcccgc ccggagcggg ccgaggaagt ggcccggcag ctgcacgccg ccggcgccgt     960
acgcacgtgg gccgtacagc tgaggaggtc cactcatgag cgctgaacag ccgtcaaccc    1020
tgctgtccgc gccgcgacgg acaccgcgac agccgttgcc cagccgaaca tcgcgctgat    1080
caagtactgg ggcaagaagg acgagcacct ggtcctgccc cgtaccgaca gcctgtcgat    1140
gactctggac atcttcccga cgaccacccg ggtccagctc gcgcccggcg ccgggcagga    1200
cacggtggcc ttcaacggcg agcccgcgac gggagaggcc gagcggcgca tcaccgcatt    1260
cctccggctg gtgcgggagc ggtcggggcg caccgaacgg gcccgcgtcg agacggagaa    1320
caccgtcccc accggggccg gcctggcctc gtcggcagc ggtttcgctg ccctcgccgt    1380
cgccgccgcc gcggcgtacg ggctcggtct cgacgcgcgg ggcctgtccc ggctggcccg    1440
acgcggctcc gggtcggcct cccggtcgat cttcgacggg ttcgccgtgt ggcacgccgg    1500
ccacgccggc ggcactcccg aggaggccga tctcggctcg tacgccgaac cggtgccggc    1560
cgtggacctg gagccggcgc tggtggtcgc ggtggtcagc gccgccccca aggcggtgtc    1620
cagccgggag gccatgcgga ggaccgtgga cacctcaccg ctgtacgagc cgtgggcggt    1680
gtccagccgg gccgacctgg cggacatcgg agccgcgctc gcccgcggca acctgccggc    1740
ggtgggcgag atcgcggagc gcaacgccct cggcatgcac gccaccatgc tggccgcacg    1800
ccccgccgtg cgctacctgt caccggcctc gctcgccgtg ctcgacggcg ttctgcagtt    1860
gcggcgggac ggcgtgccgg cctacgcgac gatggacgcc ggtcccaacg tgaaggtgct    1920
ctgcccgcgt tcggacgccg agcgggtcgc ggaagccctg cgcgccgccg cgccggtcgg    1980
```

```
agcggtgcac atcgccggtc cggggcgggg tgcccgcctg gtggcggagg aatgccggtg    2040
accggcccgc gcgcggtgac ccggcgcgcc ccgggcaagc tcttcgtcgc gggtgaatac    2100
gcggtggtgg aaccgggcaa ccgggcgatc ctggtggcag tcgaccggta cgtcaccgtc    2160
accgtgtccg acgcgccgc acccgtgtc gtcgtctcct ccgacatcgg agccggcccg      2220
gtgcaccacc cgtggcagga cgggcggctg acaggcggta cgggcacacc tcatgtggtg    2280
gcggcggtcg agaccgtggc ccgcctcctg gccgaacgcg gccggtccgt cccgccgttg    2340
gggtggtcga tcagcagcac gctgcacgag gacggccgga agttcggact gggctccagc    2400
ggcgcggtga cggtggcgac ggtcagtgcc gtcgcagccc attgcggact ggaactcacc    2460
gccgaagaac gcttccggac ggcgctgatc gcctccgccc gcatcgaccc caggggatcc    2520
ggcggagaca tcgccaccag cacctggggc ggctggatcg cctaccgggc gcccgaccgg    2580
gacgccgtac tcgacttgac ccgccgtcag ggggtcgacg aggcactccg ggcgccgtgg    2640
ccgggcttct ccgtacgact gtcgccgccc cggaacctct gcctcgaggt cggctggacc    2700
ggcaaccccg tgtccaccac gtccctcctg acggacctgc atcggcgcac ctggcggggc    2760
agccccgcgt accggaggta cgtcggggcg accggcgagc tcgtggacgc cgcagtcatc    2820
gcgctggagg acgcgacac cgagggcctg ttgcggcagg tccggcgggc ccgtcacgag    2880
atggtccgcc tcgacgacga ggtcggcctc ggcatcttca ccccgaact gacggccctc      2940
tgcgccatcg ccgaacgcgc cggcgcgcc aagccctcgg gggccggggg cggcgactgc      3000
ggcatcgcgc tgctggacgc cgaggcccgc tacgaccgct caccgttgca ccggcaatgg    3060
gccgcggccg gggtgctgcc gctactggtg tcgcctgcca cggaaggagt cgaggaatga    3120
gcagtgccca gcgcaaggac gaccatgtcc ggctcgccac ggagcagcag cgcgcgcaca    3180
gcggacgcaa ccagttcgac gacgtgtcgt tcgtccacca cgccctcgcc ggaatcgacc    3240
ggccggacgt ccgcctggcc acgacgttcg ccggcatcac ctggcgactg ccgctgtaca    3300
tcaacgcgat gacgggcggc agcgccaaga ccggcgccat caaccgggac ctggccgtcg    3360
ccgccaggga gaccggcgcc gccatcgcgt ccgggtccat gcacgccttt tcagggacc     3420
cctcctgcgc ggacaccttc cgcgtgctgc gcaccgagaa ccccgacggt ttcgtgatgg    3480
cgaacgtcaa cgcgaccgcg tccgtcgaca acgcccgccg ggccgtcgac ctgatcgagg    3540
cgaacgccct gcagatccac ctgaacacgg cgcaggagac gcccatgccg gagggcgacc    3600
ggtcgttcgg gtcgtggccg gcccagatcg cgaagatcac ggcggccgtc gacgtcccgg    3660
tgatcgtcaa ggaggtcggc aacgggctca gcaggcagac cctcctggcg ctgccggatc    3720
tgggggtccg ggtcgccgac gtcagcggcc gcggcggcac cgacttcgcc cgtatcgaga    3780
acagccggcg ccccctgggc gactacgcct tcctgcacgg ctgggggcag tccaccccgg    3840
cctgtctgct ggacgctcag gacgtcggct tccccctgct ggcctccggt gggatccgca    3900
acccgctcga cgtcgcccgg gcgctcgcgc tcggcgccgg cgcgtgggc tcctcgggcg      3960
tattcctgcg cacgctgatc gacgggggcg tatccgccct ggtcgcacag atctccacct    4020
ggctggacca gctcgccgcg ctgcagacca tgctcggtgc gcggaccccc gccgacctca    4080
cccgctgcga cgtgctgatc cacggcccgc tccggtcctt ctgcacggac cggggcatag    4140
acatcgggcg gttcgcccgg cgcagcagct ccgccgacat ccgttccgag atgacaggaa    4200
gcacacgatg accgaagcgc acgccaccgc cggcgtcccg atgcggtggg tggggcccgt    4260
ccgcatctcg gaaacgtcg ccaccatcga aacccaggtg ccgctggcca cgtacgagtc      4320
tccgctctgg ccttcggtgg gccgcggcgc gaaggtgtcc cggctgaccg agaagggcat    4380
```

-continued

```
cgtcgccacg ctcgtcgacg agcgcatgac ccgttccgtg ctcgtcgagg cgaccgacgc   4440
gctcaccgcg ctctccgcgg cacgaccat cgaggcccgc atcgacgagc tgcgcgagct    4500
ggtgcgcggc tgcagccggt tcgcccagct gatcggcatc cggcacgaga tcaccggaaa   4560
cctgctgttc gtccggttcg agttcagcac cggtgacgcc tccgggcaca acatggcgac   4620
cctggcttcc gacgtgctcc tccagcatct gctggaaacg gttcccggca tctcctacgg   4680
gtcgatctcc gggaactact gcacggacaa gaaggccacc gccatcaacg gcatcctggg   4740
ccgcggcaag aacgtcgtca ccgagctgct cgtgccgcgt gacgtggtgg ccgacgtcct   4800
gaacaccacc gccgcgaaga tcgccgagct gaacctccgc aagaacctgc tcgggacact   4860
tctcgcaggc ggcatccggt cggcgaacgc ccactacgcg aacatgctgc tcgcgttcta   4920
cctggcgacc ggtcaggacg cggcgaacat cgtcgagggc tcccagggcg tcgtcacggc   4980
cgaggaccgc gacggcgacc tctacttagc ctgcacactg ccgaacctca tcgtcggcac   5040
ggttggcaac ggcaagggcc tgggcttcgt ggagaccaac ctgaaccggc tcggctgccg   5100
tgcggaccgc gagcccggcg agaacgcccg ccggctcgcc gtcatcgcgg cggccacggt   5160
gctctgcggg gagctgtcgc tgctcgcggc gcagaccaac cccggcgaac tgatgcgtgc   5220
gcatgtccaa ctggaacgag gccacacgac cgcgaaggct ggtgtctaga gcatgcccct   5280
cgccataggc atccatgatc tgtcgttcgc caccggcgag ttcggctgcc gcacaccgcc   5340
ctcgccgctc acaacggaac cgagatcggc aagtaccacg cgggcatcgg ccaggagtcg   5400
atgagcgtcc cggccgccga cgaggacatc gtgaccctgg ccgcgacggc tgccgcaccg   5460
atcgtcgccc ggcacggcag cgaccggatc cgcacggtcg tgctcgcgac cgaatcgtcg   5520
atcgaccagg cgaagtcggc cggtgtgtac gtccactccc tgctcggact gccgtcggcc   5580
acccgcgtcg tggagctgaa gcaggcctgt tacggggcca cggccggcct gcagttcgcc   5640
atcggtctgg tgcagcgcga ccccgcccag caggttctcg tcatcgccag tgacgtctcc   5700
aagtacgacc tggacagccc cggtgaggcg acgcaggggcg ccgccgcggt cgccatgctc   5760
gtaggcgccg atccgggggct ggtgcggatc gaggatccgt cgggcctgtt caccgtcgac   5820
gtcatggact tctggcggcc gaactaccgc accacggctc tggtcgacgg ccaggaatcc   5880
atcggcgcct acctccaggc ggtggagggg gcctggaagg actactcgga gcggggcggc   5940
cactccctgg agcagttcgc cgcgttctgc taccaccagc cgttcaccaa gatggctcac   6000
aaggcccacc ggcacctgct gaactactgc agccacgaca tccaccacga cgacgtcacg   6060
cgtgccgtcg gccggaccac cgcctacaac agggtgatcg ggaacagcta caccgcgtcc   6120
gtctacctgg gcctcgccgc gctcctcgac caggccgacg acctgaccgg tgagcgcatc   6180
ggattcctca gctacggttc cggcagcgtc gccgagttct tcggcgggat cgtcgtcgcc   6240
ggataccggg accggctgcg gacgcggcg aacatcgagg ccgtctcccg gcgacggccc   6300
atcgactacg ccggctaccg cgagctgcac gagtgggcct tccccgcccg acggggagcc   6360
cactccaccc cgcagcagac cacgggaccg ttccggctgt ccggtatcag cggccacaag   6420
cgcctctacc gagcgtgctg a                                            6441
```

<210> SEQ ID NO 30
<211> LENGTH: 2710
<212> TYPE: DNA
<213> ORGANISM: Solanum laciniatum

<400> SEQUENCE: 30

-continued

```
catatgagtt ctttggttct tcaatgttgg aaattatcat ctccatctct gattttacaa      60
caaaatacat caatatccat gggtgcattc aaaggtattc ataaacttca aatcccaaat     120
tcgcctctga cagtgtctgc tcgtggactc aacaagattt catgctcact caacttacaa     180
accgaaaagc tttgttatga ggataatgat aatgatcttg atgaagaact tatgcctaaa     240
cacattgctt tgataatgga tggtaatagg agatgggcaa aggataaggg tttagaagta     300
tatgaaggtc acaaacatat tattccaaaa ttaaaagaga tttgtgacat ttcttctaaa     360
ttgggaatac aaattatcac tgcttttgca ttctctactg aaaattggaa acgatccaag     420
gaggaggttg atttcttgtt gcaaatgttc gaagaaatct atgatgagtt ttcgaggtct     480
ggagtaagag tgtctattat aggttgtaaa tccgacctcc caatgacatt acaaaaatgc     540
atagcattaa cagaagagac tacaaagggc aacaaaggac ttcaccttgt gattgcacta     600
aactatggtg gatattatga catattgcaa gcaacaaaaa gcattgttaa taaagcaatg     660
aatggtttat tagatgtaga agatatcaac aagaatttat ttgatcaaga acttgaaagc     720
aagtgtccaa atcctgattt acttataagg acaggaggtg aacaaagagt tagtaacttt     780
ttgttgtggc aattggctta cactgaattt tacttcacca acacattgtt tcctgatttt     840
ggagaggaag atcttaaaga ggcaataatg aacttttcaac aaaggcatag acgttttggt     900
ggacacacat attgatccgc gcacgacact gaacatacga atttaaggaa taaagataat     960
gtctaccatt attgcgatac aagtgttgct tcctattcca actactaaaa catacccctag   1020
tcatgacttg gagaagtcct cttcgcggtg tcgctcctcc tccactcctc gccctagact    1080
gtgttgctcg ttgcaggtga gtgatccgat cccaacgggc cggcgatccg gaggctaccc    1140
gcccgcccta tgggatttcg acactattca atcgctcaac accgagtata agggagagag    1200
gcacatgaga agggaagaag acctaattgg gcaagttaga gagatgctgg tgcatgaagt    1260
agaggatccc actccacagc tggagttcat tgatgatttg cataagcttg gcatatcttg    1320
ccattttgag aatgaaatcc tccaaatctt gaaatccata tatcttaatc aaaactacaa    1380
aagggatttg tactcaacat ctctagcatt cagactcctc agacaatatg gcttcatcct    1440
tccacaagaa gtatttgatt gtttcaagaa tgaggagggt acggatttca agccaagctt    1500
cggccgtgat atcaaaggct tgttacaatt gtatgaagct tctttcctat caagaaaagg    1560
agaagaaact ttacaactag caagagagtt tgcaacaaag attctgcaaa agaagttga    1620
tgagagagag tttgcaacca agatggagtt cccttctcat tggacggttc aaatgccgaa    1680
tgcaagacct ttcatcgatg cttaccgtag gaggccggat atgaatccag ttgtgctcga    1740
gctagccata cttgatacaa atatagttca agcacaattt caagaagaac tcaaagagac    1800
ctcaaggtgg tgggagagta caggcattgt ccaagagctt ccatttgtga gggataggat    1860
tgtggaaggc tactttttgga cgattggagt gactcagaga cgcgagcatg gatacgaaag    1920
aatcatgacc gcaaaggtta ttgccttagt aacatgttta gacgacatat acgatgttta    1980
tggcacgata gaagagcttc aacttttcac aagcacaatc caaagatggg atttggaatc    2040
aatgaagcaa ctccctacct acatgcaagt aagctttctt gcactacaca actttgtaac    2100
cgaggtggct tacgatactc tcaagaaaaa gggctacaac tccacaccat atttaagaaa    2160
aacgtgggtg gatcttgttg aatcatatat caaagaggca acttggtact acaacggtta    2220
taaacctagt atgcaagaat accttaacaa tgcatggata tcagtcggaa gtatggctat    2280
actcaaccac ctcttcttcc ggttcacaaa cgagagaatg cataaatacc gcgatatgaa    2340
ccgtgtctcg tccaacattg tgaggcttgc tgatgatatg gaacatcat  tggctgaggt    2400
```

```
ggagagaggg gacgtgccga aagcaattca atgctacatg aatgagacga atgcttctga    2460
agaagaagca agagaatatg taagaagagt catacaggaa gaatgggaaa agttgaacac    2520
agaattgatg cgggatgatg atgatgatga tgattttaca ctatccaaat attactgtga    2580
ggtggttgct aatcttacaa gaatggcaca gtttatatac caagatggat cggatggctt    2640
cggcatgaaa gattccaagg ttaatagact gctaaaagag acgttgatcg agcgctacga    2700
ataaggtacc                                                          2710
```

RECOMBINANT CELL, AND METHOD FOR PRODUCING β-PHELLANDRENE

TECHNICAL FIELD

The present invention relates to a recombinant cell capable of producing β-phellandrene, and a method for producing β-phellandrene using the recombinant cell.

BACKGROUND ART

Monoterpene is a generic name for compounds having 10 carbons according to the isoprene rule, biologically generated from geranyl pyrophosphate (GPP) in which dimethylallyl diphosphate (DMAPP) and isopentenyl diphosphate (IPP) are condensed, as a precursor. Over 900 kinds of monoterpene are known at present.

Monoterpene has fragrances of roses or citrus fruits, and are commonly used in perfume and so on. For example, limonene is an aroma constituent contained in citrus fruits such as lemon, and is also used as a solvent or a material for an adhesive. Menthol has refreshing fragrance, and is used as a refrigerant in confectionary and pharmaceuticals. On the other hand, in the resin industry, β-pinene, α-pinene, limonene, α-phellandrene and the like are considered as monomer materials for adhesives and transparent resins (Non-Patent Document 1).

For β-phellandrene which is one kind of monoterpene, application as a new polymer material is expected. β-phellandrene can possibly provide a polymer of higher molecular weight than α-phellandrene. However, when β-phellandrene is obtained by a synthetic chemical technique, generation of α-phellandrene which is an isomer thereof is inevitable, and separation of these isomers is very difficult (Non-Patent Document 2). Therefore, it is difficult to obtain β-phellandrene with high purity, and this makes it difficult to examine the polymer properties and the like of β-phellandrene.

On the other hand, as the biosynthesis pathway of β-phellandrene, geranyl pyrophosphate (GPP) or neryl pyrophosphate (NPP) is biosynthesized from isopentenyl diphosphate (IPP) under the action of geranyl pyrophosphate (GPP) synthase or neryl pyrophosphate (NPP) synthase. Sequentially, under the action of β-phellandrene synthase, β-phellandrene is biosynthesized from GPP or NPP. In tomato and lavender, β-phellandrene synthase is found (Non-Patent Documents 3 and 4).

Patent Document 1 discloses a method for producing monoterpene using a transformant of C1 metabolism host cell into which a nucleic acid encoding cyclic terpene synthase is introduced. As an example thereof, an experiment example of producing limonene using a transformant of Methylomonas bacterium is described. Although β-phellandrene is referred, an example thereof is not given. Although β-phellandrene synthase is referred, a concrete example and an acquiring method of β-phellandrene synthase and its gene, and a concrete configuration and a construction method of a transformant capable of producing β-phellandrene are not shown.

PRIOR ART DOCUMENTS

Patent Document

Patent Document 1: JP 2005-500805 A

Non-Patent Documents

Non-Patent Document 1: Satou K., et al., Green Chemistry 2006, 8, 878-882

Non-Patent Document 2: Mori K., Tetrahedron: Asymmetry 2006, 17, 2133-2142

Non-Patent Document 3: Demissie, Z. A., et al., Planta. 2011, 233, 685-96.

Non-Patent Document 4: Schilmiller, A. L., et al., Proc Natl Acad Sci USA., 2009, 106, 10865-70.

DISCLOSURE OF INVENTION

Technical Problem

In light of the above, an object of the present invention is to provide a series of techniques for obtaining β-phellandrene with high purity and in a large quantity.

Solutions to Problem

One aspect of the present invention for solving the aforementioned problem is a recombinant cell capable of producing β-phellandrene prepared by introducing at least one nucleic acid selected from the group consisting of a nucleic acid encoding geranyl pyrophosphate synthase and a nucleic acid encoding neryl pyrophosphate synthase, and a nucleic acid encoding β-phellandrene synthase into a host cell in such a manner that these nucleic acids are expressed in the host cell.

The present invention relates to a recombinant cell capable of producing β-phellandrene. The recombinant cell of the present invention is prepared by introducing "at least one nucleic acid selected from the group consisting of a nucleic acid encoding geranyl pyrophosphate (GPP) synthase and a nucleic acid encoding neryl pyrophosphate (NPP) synthase", and "a nucleic acid encoding β-phellandrene synthase" into a host cell, and these nucleic acids are expressed in the host cell. In other words, in the recombinant cell of the present invention, the ability to express GPP synthase and/or NPP synthase and the ability to express β-phellandrene synthase are newly added or enhanced with respect to the host cell.

In the recombinant cell of the present invention, GPP is synthesized from isopentenyl diphosphate (IPP) under the action of GPP synthase expressed in the cell, and/or NPP is synthesized from IPP under the action of NPP synthase expressed in the cell. Further, β-phellandrene is synthesized from GPP and/or NPP under the action of β-phellandrene synthase expressed in the cell. Therefore, by culturing the recombinant cell of the present invention, it is possible to produce β-phellandrene with high purity and in large quantity.

Preferably, the host cell does not have methane monooxygenase.

Preferably, the host cell is *Escherichia coli* or yeast.

With this configuration, it is possible to easily culture the recombinant cell in large scale.

Preferably, 10 mg or more of β-phellandrene can be produced per 1 g of wet cells of the recombinant cell Preferably, the nucleic acid encoding geranyl pyrophosphate synthase encodes the following protein (a), (b) or (c):

(a) protein consisting of an amino acid sequence represented by SEQ ID NO: 2, (b) protein consisting of an amino acid sequence in which 1 to 20 amino acids are deleted, substituted or added in the amino acid sequence represented by SEQ ID NO: 2, and having geranyl pyrophosphate synthase activity, or (c) protein consisting of an amino acid sequence having a homology of 60% or more with the amino acid sequence represented by SEQ ID NO: 2, and having geranyl pyrophosphate synthase activity.

Preferably, the nucleic acid encoding neryl pyrophosphate synthase encodes the following protein (d), (e) or (f):

(d) protein consisting of an amino acid sequence represented by SEQ ID NO: 4, (e) protein consisting of an amino acid sequence in which 1 to 20 amino acids are deleted, substituted or added in the amino acid sequence represented by SEQ ID NO: 4, and having neryl pyrophosphate synthase activity, or (f) protein consisting of an amino acid sequence having a homology of 60% or more with the amino acid sequence represented by SEQ ID NO: 4, and having neryl pyrophosphate synthase activity.

Preferably, the nucleic acid encoding β-phellandrene synthase encodes the following protein (g), (h) or (i):

(g) protein consisting of an amino acid sequence represented by SEQ ID NO: 6 or 8, (h) protein consisting of an amino acid sequence in which 1 to 20 amino acids are deleted, substituted or added in the amino acid sequence represented by SEQ ID NO: 6 or 8, and having β-phellandrene synthase activity, or (i) protein consisting of an amino acid sequence having a homology of 60% or more with the amino acid sequence represented by SEQ ID NO: 6 or 8, and having β-phellandrene synthase activity.

Preferably, a nucleic acid encoding at least one enzyme that acts in a synthesis pathway of isopentenyl diphosphate is further introduced, and the nucleic acid is expressed in the host cell.

With such a configuration, IPP which is to be a substrate for GPP synthase or NPP synthase is supplied efficiently.

Preferably, the synthesis pathway of isopentenyl diphosphate is a mevalonate pathway.

Preferably, the mevalonate pathway is a mevalonate pathway of yeast or *actinomyces*.

Another aspect of the present invention is a method for producing β-phellandrene by culturing the recombinant cell to produce β-phellandrene in the recombinant cell.

The present invention relates to a method for producing β-phellandrene. In the present invention, by culturing the recombinant cell, β-phellandrene is produced in the recombinant cell. According to the present invention, it is possible to produce β-phellandrene with high purity and in large quantity.

Preferably, 10 mg or more of β-phellandrene is produced per 1 g of wet cells of the recombinant cell.

Preferably, β-phellandrene released outside the recombinant cell is collected.

Preferably, β-phellandrene is collected from a gas phase of a culture system of the recombinant cell.

Advantageous Effect of Invention

According to the present invention, it is possible to produce β-phellandrene with high purity and in large quantity.

BRIEF DESCRIPTION OF DRAWINGS

FIGS. 1A and 1B are total ion chromatograms of GC-MS analysis conducted for the gas phase fraction of the culture conducted in Example 5, wherein FIG. 1A shows the case of a control recombinant, and FIG. 1B shows the case of a recombinant capable of producing β-phellandrene.

FIGS. 2A-2C are mass spectrums showing the results of peaks in FIG. 1B identified by GC-MS, wherein FIG. 2A shows the case of peak A (β-phellandrene), FIG. 2B shows the case of peak B (limonene), and FIG. 2C shows the case of peak C (myrcene).

DESCRIPTION OF EMBODIMENT

Figure 1A:
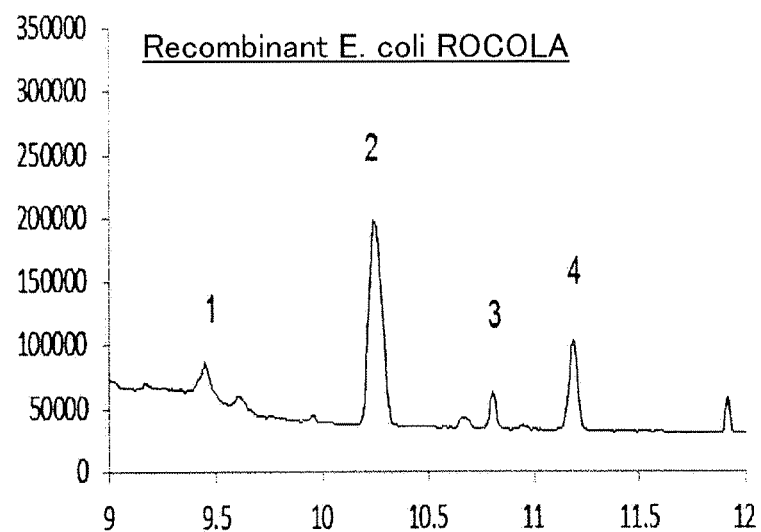

The recombinant cell of the present invention is prepared by introducing at least one nucleic acid selected from the group consisting of a nucleic acid encoding geranyl pyrophosphate (GPP) synthase and a nucleic acid encoding neryl pyrophosphate (NPP) synthase, and a nucleic acid encoding β-phellandrene synthase into a host cell in such a manner that these nucleic acids are expressed in the host cell, and the recombinant cell is capable of synthesizing β-phellandrene.

GPP synthase is not particularly limited as far as it can exert its enzyme activity in the recombinant cell. The same applies also to the nucleic acid (gene) encoding GPP synthase, and the nucleic acid is not particularly limited as far as it is normally transcribed and translated in the recombinant cell.

The same applies to NPP synthase, β-phellandrene synthase, and nucleic acids encoding these enzymes.

Concrete examples of GPP synthase include those derived from *Arabidopsis thaliana* (GenBank Accession No.: Y17376/At2g34630; Bouvier, F., et al., Plant J., 2000, 24, 241-52.), and those derived from *Mycobacterium tuberculosis* (GenBank Accession No.: NP_215504; Mann, F. M., et al., FEBS Lett., 2011, 585, 549-54.).

SEQ ID NO: 1 represents a nucleotide sequence of nucleic acid (DNA) encoding GPP synthase derived from *Arabidopsis thaliana*, and an amino acid sequence corresponding to this, and SEQ ID NO: 2 represents only the amino acid sequence. DNA having the nucleotide sequence represented by SEQ ID NO: 1 is one example of the nucleic acid encoding GPP synthase.

Further, the nucleic acid encoding GPP synthase includes at least a nucleic acid encoding the following protein (a), (b) or (c):

(a) protein consisting of an amino acid sequence represented by SEQ ID NO: 2, (b) protein consisting of an amino acid sequence in which 1 to 20 amino acids are deleted, substituted or added in the amino acid sequence represented by SEQ ID NO: 2, and having geranyl pyrophosphate synthase activity, or (c) protein consisting of an amino acid sequence having a homology of 60% or more with the amino acid sequence represented by SEQ ID NO: 2, and having geranyl pyrophosphate synthase activity.

The homology of amino acid sequence in (c) is more preferably 80% or more, further preferably 90% or more, particularly preferably 95% or more.

Concrete examples of NPP synthase include those derived from tomato (*Solanum lycopersicum*) (GenBank Accession No.: FJ797956) and so on.

SEQ ID NO: 3 represents a nucleotide sequence of nucleic acid (DNA) encoding the NPP synthase derived from tomato and an amino acid sequence corresponding to this, and SEQ ID NO: 4 represents only the amino acid sequence. DNA having the nucleotide sequence represented by SEQ ID NO: 3 is one example of the nucleic acid encoding NPP synthase.

Further, the nucleic acid encoding NPP synthase includes at least a nucleic acid encoding the following protein (d), (e) or (f):

(d) protein consisting of an amino acid sequence represented by SEQ ID NO: 4, (e) protein consisting of an amino acid sequence in which 1 to 20 amino acids are deleted, substituted or added in the amino acid sequence represented by SEQ ID NO: 4, and having neryl pyrophosphate synthase activity, or (f) protein consisting of an amino acid sequence having a homology of 60% or more with the amino acid sequence represented by SEQ ID NO: 4, and having neryl pyrophosphate synthase activity.

The homology of amino acid sequence in (f) is more preferably 80% or more, further preferably 90% or more, particularly preferably 95% or more.

In the recombinant cell of the present invention, either one nucleic acid or both nucleic acids of "nucleic acid encoding geranyl pyrophosphate (GPP) synthase" and "nucleic acid encoding neryl pyrophosphate (NPP) synthase" may be introduced.

Concrete examples of β-phellandrene synthase and a nucleic acid encoding the same include those derived from tomato (*Solanum lycopersicum*) (GenBank Accession No.: FJ797957; Schilmiller, A. L., et al., Proc Natl Acad Sci USA., 2009, 106, 10865-70.), and those derived from lavender (*Lavandula angustifolia*) (GenBank Accession No.: HQ404305; Demissie, Z. A., et al., Planta, 2011, 233, 685-96).

SEQ ID NO: 5 represents a nucleotide sequence of a nucleic acid (DNA) encoding the β-phellandrene synthase derived from tomato, and a corresponding amino acid sequence, and SEQ ID NO: 6 represents only the amino acid sequence.

SEQ ID NO: 7 represents a nucleotide sequence of a nucleic acid (DNA) encoding the β-phellandrene synthase derived from lavender, and a corresponding amino acid sequence, and SEQ ID NO: 8 represents only the amino acid sequence.

DNA having the nucleotide sequence represented by SEQ ID NO: 5 or SEQ ID NO: 7 is one example of the nucleic acid encoding β-phellandrene synthase.

Further, the nucleic acid encoding β-phellandrene synthase includes at least a nucleic acid encoding the following protein (g), (h) or (i):

(g) protein consisting of an amino acid sequence represented by SEQ ID NO: 6 or 8, (h) protein consisting of an amino acid sequence in which 1 to 20 amino acids are deleted, substituted or added in the amino acid sequence represented by SEQ ID NO: 6 or 8, and having β-phellandrene synthase activity, or (i) protein consisting of an amino acid sequence having a homology of 60% or more with the amino acid sequence represented by SEQ ID NO: 6 or 8, and having β-phellandrene synthase activity.

The homology of amino acid sequence in (i) is more preferably 80% or more, further preferably 90% or more, particularly preferably 95% or more.

The host cell in the recombinant cell of the present invention is not particularly limited, and may be a procaryotic cell or a eucaryotic cell. Examples of a procaryotic cell include bacteria and *actinomyces*. Examples of bacteria include *Escherichia* bacteria such as *Escherichia coli*, *Bacillus* bacteria such as *Bacillus subtilis*, *Pseudomonas* bacteria, cyanobacteria, *Clostridium* bacteria, *Corynebacterium* bacteria, and *Ralstonia* bacteria. Among these, *Escherichia coli* which is easy to be cultured in large scale is particularly preferred.

Examples of a eucaryotic cell include yeast, filamentous fungus, eucaryotic microalgae, a vegetable cell, and an animal cell.

Examples of yeast include *Saccharomyces cerevisiae, Schizosaccharomyces pombe, Saccharomyces uvarum, Saccharomyces carlsbergensis, Saccharomyces diastaticus, Candida tropicalis, Candida maltosa, Candida parapsilosis, Pichia pastoris, Pichia farinosa, Pichia pinus, Pichia varijii, Pichia fermentans, Pichia guilliermondii, Pichia stipitis, Saccharomyces elluris, Candida utilis, Candida guilliermondii, Hansenula henricii, Hansenula capsulata, Hansenula polymorpha, Hansenula saturnus, Lypomyces kononenkoae, Kluyveromyces marxianus, Candida lipolytica, Saccharomycopsis fibuligera, Saccharomycodes ludwigii, Saccharomyces kluyveri, Tremellamesenterica, Zygosaccharomyces acidofaciens, Zygosaccharomyces fermentati, Yarrowia lipolytica*, and *Zygosaccharomyces soja*. Among these, yeast which is easy to be cultured in large scale is particularly preferably selected.

Preferably, the host cell does not have methane monooxygenase (EC 1.14.13.25).

The method for introducing the nucleic acids respectively encoding GPP synthase, NPP synthase, and β-phellandrene synthase into the host cell is not particularly limited, and can be appropriately selected depending on the kind of the host cell or the like. For example, a vector that can be introduced into the host cell and can allow expression of the nucleic acid incorporated therein may be used.

For example, when the host cell is a prokaryote such as a bacterium, a vector that can self duplicate or can be incorporated in chromosome in the host cell, and contains a promoter at the position allowing transcription of the inserted nucleic acid (DNA) can be used. For example, it is preferred to construct in the host cell a series of structures including a promoter, a ribosome binding sequence, the above nucleic acid (DNA) and a transcription termination sequence by using the vector.

As a vector that can be used when the host cell is *E. coli*, a so-called multi copy type vector is preferred, and plasmid having a replication origin derived from ColE1, for example, pUC-series plasmids, pBR322-series plasmids or derivatives thereof are recited. More concrete examples include pUC19 [Gene, 33, 103 (1985)], pUC18, pBR322, pHelix1 (available from Roche Diagnostics), pKK233-2 (available from Amersham-Pharmacia Biotech), pSE280 (available from Invitrogen), pGEMEX-1 (available from Promega), pQE-8 (available from QIAGEN), pET-3 (available from Novagen), pBluescriptII SK(+), pBluescript II KS(+) (available from Stratagene), pSTV28 (available from TAKARA BIO INC), and pUC118 (available from TAKARA BIO INC). The promoter on the vector may be any promoter as far as it can operate in the host cell such as *E. coli*. For example, promoters derived from *E. coli* or phage such as trp promoter (Ptrp), lac promoter (Plac), PL promoter, PR promoter or the like, and T7 promoter or the like, and promoters that are artificially designed and modified, such as tac promoter and lacT7 promoter may be used.

Basically the same applies to the case where the host cell is yeast, and the vector is preferably structured to have a replication system for stable conservation in the host yeast, a promoter capable of transcribing the inserted nucleic acid (DNA), and a terminator sequence. For example, the vector may be a plasmid that can be replicated in the host yeast or can be incorporated into the host chromosome. The vector can encode expression of repeated copies of a desired DNA sequence each separated by a selective cutting site.

While the kind of the promoter that can operate in yeast is not particularly limited, for example, promoter of isocitrate lyase gene, AOX1 promoter, GAPDH promoter, PHO5 promoter, glyceraldehyde-3-phosphate dehydrogenase (TDH3) promoter, ADHI promoter, MFα1 promoter, and GAL10 promoter can be used.

When the nucleic acids are introduced into a host cell by using a vector, the nucleic acids may be incorporated into one vector, or may be incorporated into different vectors. When a plurality of nucleic acids are incorporated into one vector, the nucleic acids may be expressed under a common promoter, or the nucleic acids may be expressed under respective promoters.

When the host cell has α-phellandrene synthase, it is preferred that α-phellandrene synthase of the host cell is knocked out in advance. However, since vegetables are only the organisms that have α-phellandrene synthase in general, this operation is not usually required when the host cell is a bacterium or yeast.

In the recombinant cell of the present invention, other nucleic acid may be introduced in addition to the nucleic acids respectively encoding GPP synthase, NPP synthase, and β-phellandrene synthase. In one embodiment, a nucleic acid encoding at least one enzyme that acts in the synthesis pathway of isopentenyl diphosphate (IPP) is further introduced, and the nucleic acid is expressed in the host cell. The introduced nucleic acid may be one kind or two or more kinds.

In general, the synthesis pathway of IPP is classified into a mevalonate pathway (MVA pathway) and a non-mevalonate pathway (MEP pathway).

The mevalonate pathway is possessed by a eukaryote, and starts with acetyl CoA. Enzymes acting in the mevalonate pathway include acetyl CoA acetyl transferase, HMG-CoA synthase, HMG-CoA reductase, mevalonate kinase, 5-phosphomevalonate kinase, and diphosphomevalonate decarboxylase in this order from the upstream side.

On the other hand, the non-mevalonate pathway is possessed by a prokaryote, a chloroplast, and a plastid, and starts with glyceraldehyde 3-phosphate (GAP) and pyruvic acid. Enzymes acting in the non-mevalonate pathway include DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase, and HMB-PP reductase in this order from the upstream side.

The "enzyme acting in the IPP synthesis pathway" encoded by the nucleic acid further introduced in the present embodiment is preferably an enzyme acting in the mevalonate pathway.

The enzyme group acting in the mevalonate pathway includes acetyl CoA acetyltransferase, HMG-CoA synthase, HMG-CoA reductase, mevalonate kinase, 5-phosphomevalonate kinase, diphosphomevalonate decarboxylase, and isopentenyl diphosphate isomerase. The nucleic acid to be introduced may be selected so that an enzyme group consisting of, for example, HMG-CoAsynthase, HMG-CoA reductase, mevalonate kinase, 5-phosphomevalonate kinase, diphosphomevalonate decarboxylase, and isopentenyl diphosphate isomerase among these is expressed in the host cell.

While the mevalonate pathway is possessed by every eukaryote, it is also found in other organisms than eukaryotes. Examples of other organisms than eukaryotes having the mevalonate pathway include *Streptomyces* sp. Strain CL190 (Takagi M. et al., J. Bacteriol. 2000, 182(15), 4153-7), *Streptomyces griseolosporeus* MF730-N6 (Hamano Y. et al., Biosci. Biotechnol. Biochem. 2001, 65(7), 1627-35) in *actinomyces*.

In bacteria, *Lactobacillus helvecticus* (Smeds A et al., DNA seq. 2001, 12(3), 187-190), *Corynebacterium amycolatum, Mycobacterium marinum, Bacillus coagulans, Enterococcus faecalis, Streptocouss agalactiae, Myxococcus xanthus* and the like are recited (Lombard J. et al., Mol. Biol. Evol. 2010, 28(1), 87-99).

In archaea, genus *Aeropyrum*, genus *Sulfolobus*, genus *Desulfurococcus*, genus *Thermoproteus*, genus *Halobacterium*, genus *Methanococcus*, genus *Thermococcus*, genus *Pyrococcus*, genus *Methanopyrus*, genus *Thermoplasma* and so on are recited (Lombard J. et al., Mol. Biol. Evol. 2010, 28(1), 87-99).

The source of the enzyme group acting in the mevalonate pathway is not particularly limited, however, the enzyme group acting in the mevalonate pathway of yeast or *actinomyces* is particularly preferably employed.

These enzymes may be naturally occurring enzymes or enzymes modified therefrom. For example, amino acid substitution variants of each enzyme, and polypeptides that are partial fragments of each enzyme and have equivalent enzyme activity are also applicable.

The method for culturing the recombinant cell of the present invention is not particularly limited, and may be appropriately conducted depending on the kind of the host cell and the like.

When the recombinant cell is aerobic or obligately anaerobic, for example, culturing in a liquid medium under aeration and stirring can be conducted.

When the recombinant cell is strictly anaerobic, for example, culturing can be conducted while the gas phase is replaced with gas such as high-purity or deoxidized nitrogen, and an appropriate amount of a reducing agent such as sodium sulfide, cysteine or the like is added to the culture liquid.

The culture medium is not particularly limited as far as it allows growth of the recombinant cell. As a principal carbon source in the culture medium, organic carbon sources such as saccharides and protein digests are preferably used. Examples of saccharides include monosaccharide (e.g. glucose), disaccharide (e.g. maltose), oligosaccharide, polysaccharide (e.g. starch), and sugar alcohol. Examples of protein digests include peptone, triptone and casamino acids.

By culturing the recombinant cell of the present invention, it is possible to produce a large quantity of β-phellandrene. As the producibility of β-phellandrene, a production amount of 10 mg or more of β-phellandrene per 1 g of wet cells can be achieved.

When the recombinant cell of the present invention is cultured to produce β-phellandrene, mixing of α-phellandrene does not substantially occur unlike the case of production by a synthetic chemical technique.

The produced β-phellandrene is released outside the recombinant cell, or accumulated in the cell. In the present invention, any of such β-phellandrene may be collected, and β-phellandrene can be collected concretely from crushed cells, the culture liquid (culture supernatant), the gas phase of the culture system or the like. Preferably, β-phellandrene released outside the cell is collected, and concretely, it is collected from the culture liquid (culture supernatant) or the gas phase of the culture system.

As a method for isolating and purifying β-phellandrene from the culture of the recombinant cell, for example, the culture liquid (culture supernatant) is extracted with an appropriate solvent such as pentane, and is further purified to high purity by chromatography such as reversed phase chromatography or gas chromatography. Since β-phellandrene released outside the cell evaporates also in the gas phase, this may be liquefied by a cold trap or the like to collect it.

In the following, the present invention will be described more specifically by way of examples. However, the present invention is not limited to these examples.

Example 1

In the present example, a recombinant *E. coli* into which NPP synthase gene from tomato and β-phellandrene synthase gene from tomato were introduced was prepared, and the recombinant *E. coli* was cultured to produce β-phellandrene.

(1) Isolation of NPP Synthase Gene Derived from Tomato

Using total RNA derived from tomato (*Solanum lycopersicum*) as a template, a nucleic acid encoding NPP synthase from tomato (NPP synthase gene from tomato, SEQ ID NO: 3, GenBank Accession No.: FJ797956) was amplified by RT-PCR using primers represented by SEQ ID NO: 9 and SEQ ID NO: 10. The obtained nucleic acid was cut with NdeI and EcoRI, and introduced into pET23a vector (available from Novagen). The nucleotide sequence of the nucleic acid introduced into the vector was examined and correctness was confirmed. In this manner, vector pT21TNPP to express NPP synthase from tomato was prepared.

(2) Isolation of β-Phellandrene Synthase Gene Derived from Tomato

Using total RNA derived from tomato as a template, a nucleic acid encoding β-phellandrene synthase from tomato (β-phellandrene synthase gene from tomato, SEQ ID NO: 5, GenBank Accession No.: FJ797957) was amplified by RT-PCR using primers represented by SEQ ID NO: 11 and SEQ ID NO: 12. The obtained nucleic acid was cut with NcoI and BamHI, and introduced into pACYCDuet-1 vector (available from Novagen). The nucleotide sequence of the nucleic acid introduced into the vector was examined and correctness was confirmed. In this manner, vector pACTPD to express β-phellandrene synthase from tomato was prepared.

(3) Preparation of Recombinant *E. coli* Capable of Producing β-Phellandrene

The expression vectors pT23TNPP and pACTPD obtained in the above (1) and (2) were introduced into *E. coli* BL21 (DE3) strain, to prepare a recombinant *E. coli* BL21BPD1 capable of producing β-phellandrene.

As controls, a recombinant *E. coli* having only pET23a vector into which a nucleic acid was not inserted, and a recombinant *E. coli* having only pACYCDuet-1 vector into which a nucleic acid was not inserted were separately prepared.

(4) Production of β-Phellandrene

The recombinant *E. coli* BL21BPD1 was cultured in a 2×YT medium (1.6% (w/v) BactoTripton, 1% (w/v) Yeast Extract, 0.5% (w/v) NaCl) containing 100 μg/mL of ampicillin and 34 μg/mL of chloramphenicol at 30° C., 110 rpm (swing) for 30 hours. At this time, the system was brought into a closed system after 16 hours from start of the culturing. After end of the culture, centrifugal separation was conducted to obtain cells and a culture supernatant.

The cells were crushed, and the supernatant of the crush liquid was extracted with pentane. The extracted fraction was analyzed by gas chromatography, and β-phellandrene was detected. The gas phase fraction was analyzed, and β-phellandrene was detected also in the gas phase.

Also the culture supernatant was extracted with pentane. This extracted fraction was analyzed by gas chromatography, and β-phellandrene was detected.

On the other hand, in the control recombinant *E. coli* into which only pET23a vector or pACYCDuet-1 vector was introduced, β-phellandrene was not detected in any of the cells, the culture supernatant, and the gas phase.

These reveal that β-phellandrene can be produced by culturing the recombinant *E. coli* into which NPP synthase gene from tomato and β-phellandrene synthase gene from tomato were introduced. The produced β-phellandrene was collectible from the cells, the culture supernatant, and the gas phase.

Example 2

In the present example, a recombinant *E. coli* into which GPP synthase gene from *Arabidopsis thaliana* and β-phellandrene synthase gene from lavender were introduced was prepared, and the recombinant *E. coli* was cultured to produce β-phellandrene.

(1) Isolation of GPP Synthase Gene Derived from *Arabidopsis thaliana*

Using total RNA derived from *Arabidopsis thaliana* as a template, a nucleic acid encoding GPP synthase from *Arabidopsis thaliana* (GPP synthase gene from *Arabidopsis thaliana*, SEQ ID NO: 1, GenBank Accession No.: Y17376) was amplified by RT-PCR using primers represented by SEQ ID NO: 13 and SEQ ID NO: 14. The obtained nucleic acid was cut with NdeI and EcoRI, and introduced into pET23a vector (available from Novagen). The nucleotide sequence of the nucleic acid introduced into the vector was examined and correctness was confirmed. In this manner, vector pT23AGPP to express GPP synthase from *Arabidopsis thaliana* was prepared.

(2) Isolation of β-Phellandrene Synthase Gene Derived from Lavender

Using total RNA derived from lavender (*Lavandula angustifolia*) as a template, a nucleic acid encoding β-phellandrene synthase from lavender (β-phellandrene synthase gene from lavender, SEQ ID NO: 7, GenBank Accession No: HQ404305) was amplified by RT-PCR using primers represented by SEQ ID NO: 15 and SEQ ID NO: 16. The obtained nucleic acid was cut with NcoI and EcoRI, and introduced into pACYCDuet-1 vector (available from Novagen). The nucleotide sequence of the nucleic acid introduced into the vector was examined and correctness was confirmed. In this manner, vector pACLPD to express β-phellandrene synthase from lavender was prepared.

(3) Preparation of Recombinant *E. coli* Capable of Producing β-Phellandrene

The expression vectors pT23AGPP and pACLPD obtained in the above (1) and (2) were introduced into *E. coli* BL21 (DE3) strain, to prepare a recombinant *E. coli* BL21BPD2 capable of producing β-phellandrene.

As controls, a recombinant *E. coli* having only pET23a vector into which a nucleic acid was not inserted, and a recombinant *E. coli* having only pACYCDuet-1 vector into which a nucleic acid was not inserted were separately prepared.

(4) Production of β-Phellandrene

Recombinant *E. coli* BL21BPD2 was cultured in a 2×YT medium containing 100 μg/mL of ampicillin and 34 μg/mL of chloramphenicol at 30° C., 110 rpm (swing) for 30 hours. At this time, the system was brought into a closed system after 16 hours from start of the culturing. After end of the culture, centrifugal separation was conducted to obtain cells and a culture supernatant.

The cells were crushed, and the supernatant of the crush liquid was extracted with pentane. The extracted fraction was analyzed by gas chromatography, and β-phellandrene was detected.

Also the culture supernatant was extracted with pentane. This extracted fraction was analyzed by gas chromatography, and β-phellandrene was detected. Also the gas phase fraction was analyzed, and β-phellandrene was detected in the gas phase.

On the other hand, in the control recombinant *E. coli* into which only pET23a vector or pACYCDuet-1 vector was introduced, β-phellandrene was not detected in any of the cells, the culture supernatant, and the gas phase.

These reveal that β-phellandrene can be produced by culturing the recombinant *E. coli* into which GPP synthase gene from *Arabidopsis thaliana* and β-phellandrene synthase gene from lavender were introduced. The produced β-phellandrene was collectible from the cells, the culture supernatant, and the gas phase.

Example 3

In this example, a recombinant yeast into which NPP synthase gene from tomato and β-phellandrene synthase gene from tomato were introduced was prepared, and the recombinant yeast was cultured to produce β-phellandrene.

(1) Isolation of NPP Synthase Gene Derived from Tomato

Using total RNA derived from tomato as a template, a nucleic acid encoding NPP synthase from tomato (NPP synthase gene from tomato, SEQ ID NO: 3, GenBank Accession No.: FJ797956) was amplified by RT-PCR using primers represented by SEQ ID NO: 13 and SEQ ID NO: 14. The obtained nucleic acid was cut with BamHI, and then introduced into pPIC3.5K vector (available from Invitrogen). The nucleotide sequence of the nucleic acid introduced into the vector was examined and correctness was confirmed. In this manner, vector pP3.5TNPP to express NPP synthase from tomato was prepared.

(2) Isolation of β-Phellandrene Synthase Gene Derived from Tomato

Using total RNA derived from tomato as a template, a nucleic acid encoding β-phellandrene synthase from tomato (β-phellandrene synthase gene from tomato, SEQ ID NO: 5, GenBank Accession No.: FJ797957) was amplified by RT-PCR using primers represented by SEQ ID NO: 19 and SEQ ID NO: 20. The obtained nucleic acid was cut with BamHI, and then introduced into pPIC3.5K vector (available from Invitrogen). The nucleotide sequence of the nucleic acid introduced into the vector was examined and correctness was confirmed. In this manner, vector pP3.5TPD to express β-phellandrene synthase from tomato was prepared.

(3) Preparation of Recombinant Yeast Capable of Producing β-Phellandrene

Methanol assimilating yeast *Pichia pastoris* GS115 strain (available from Invitrogen) was transformed with a mixture of equal parts of the expression vectors pP3.5TNPP and pP3.5TPD obtained in the above (1) and (2). The transformation was conducted according to the manual (No. 25-0156, No. 25-0043) provided from Invitrogen. To obtain multiple copies of transductant, Geneticin (available from Invitrogen) tolerant strain at a concentration of 1.5 mg/mL was obtained. In this manner, a recombinant yeast GSNP-1 having respective multiple copies of NPP synthase gene from tomato and β-phellandrene synthase gene from tomato was obtained.

As a control, Geneticin (available from Invitrogen) tolerant strain at a concentration of 1.5 mg/mL having only pPIC3.5K vector into which a nucleic acid was not inserted was obtained (recombinant yeast GS115).

(4) Production of β-Phellandrene

After pre-culturing GSNP-1 in a MGY medium (1.34% (w/v) YNB, 1% (w/v) glycerol, $4 \times 10^{-5}$% (w/v) biotin; YMB: 13.4% (w/v) yeast nitrogen base, 10% (w/v)ammonium sulfate) (manual of Invitrogen No. 25-0043), cells were collected, and the collected cells were main-cultured in a Fermentation basal salts medium (85% Phosphoric acid 26.7 ml, Calcium sulfate 0.093% (w/v), Potassium sulfate 1.82% (w/v), Magnesiumsulfate-7H$_2$O 1.49% (w/v), Potassium hydroxide 0.413% (w/v), Glycerol 4.0% (w/v)) (manual of Invitrogen Ver. B 053002) for 64 hours. At this time, the system was brought into a closed system after 24 hours from start of the culturing. For inducing expression of the introduced enzyme genes, 1/200-volume of 100% methanol was added to the culture liquid after lapses of 24 hours and 48 hours from starting of the culture. After end of the culture, the cells and a culture supernatant were collected by centrifugal separation.

The cells were crushed by a glass bead method (manual of Invitrogen No. 25-0043) and a supernatant was obtained. A pentane extract of the supernatant was analyzed by gas chromatography, and β-phellandrene was detected.

Also the culture supernatant was extracted with pentane. The extracted fraction was analyzed by gas chromatography, and β-phellandrene was detected. Also the gas phase fraction was analyzed, and β-phellandrene was detected in the gas phase.

On the other hand, in the control recombinant yeast GS115 into which only pPIC3.5K vector was introduced, β-phellandrene was not detected in any of the cells, the culture supernatant, and the gas phase.

These reveal that β-phellandrene can be produced by culturing the recombinant yeast into which NPP synthase gene from tomato and β-phellandrene synthase gene from tomato were introduced. The produced β-phellandrene was collectible from the cells, the culture supernatant, and the gas phase.

Example 4

In this example, a recombinant yeast into which GPP synthase gene from *Arabidopsis thaliana* and β-phellandrene synthase gene from lavender were introduced was prepared, and the recombinant yeast was cultured to produce β-phellandrene.

(1) Isolation of GPP Synthase Gene Derived from *Arabidopsis thaliana*

Using total RNA derived from *Arabidopsis thaliana* as a template, a nucleic acid encoding GPP synthase from *Arabidopsis thaliana* (GPP synthase gene from *Arabidopsis thaliana*, SEQ ID NO: 1, GenBank Accession No.: Y17376) was amplified by RT-PCR using primers represented by SEQ ID NO: 21 and SEQ ID NO: 22. The obtained nucleic acid was cut with BamHI, and then introduced into pPIC3.5K vector (available from Invitrogen). The nucleotide sequence of the nucleic acid introduced into the vector was examined and correctness was confirmed. In this manner, vector pP3.5AGPP to express GPP synthase from *Arabidopsis thaliana* was prepared.

(2) Isolation of β-Phellandrene Synthase Gene Derived from Lavender

Using total RNA derived from lavender as a template, a nucleic acid encoding β-phellandrene synthase from lavender (β-phellandrene synthase gene from lavender, SEQ ID NO: 7, GenBank Accession No.: HQ404305) was amplified by RT-PCR using primers represented by SEQ ID NO: 23 and SEQ ID NO: 24. The obtained nucleic acid was cut with EcoRI, and then introduced into pPIC3.5K vector (available from Invitrogen). The nucleotide sequence of the nucleic acid introduced into the vector was examined and correctness was confirmed. In this manner, vector pP3.5LPD to express β-phellandrene synthase from lavender was prepared.

(3) Preparation of Recombinant Yeast Capable of Producing β-Phellandrene

Methanol assimilating yeast *Pichia pastoris* GS115 strain (available from Invitrogen) was transformed with a mixture of equal parts of the expression vectors pP3.5AGPP and pP3.5LPD obtained in the above (1) and (2). The transformation was conducted according to the manual (No. 25-0156, No. 25-0043) provided from Invitrogen. To obtain multiple copies of transductant, Geneticin (available from Invitrogen) tolerant strain at a concentration of 1.5 mg/mL was obtained. In this manner, a recombinant yeast GSNP-2 having respective multiple copies of GPP synthase gene from *Arabidopsis thaliana* and β-phellandrene synthase gene from lavender was obtained.

(4) Production of β-Phellandrene

After pre-culturing GSNP-2 in a MGY medium (manual of Invitrogen No. 25-0043), cells were collected, and the collected cells were main-cultured in a Fermentation basal salts medium (manual of Invitrogen Ver. B 053002) for 64 hours. For inducing expression of the introduced enzyme genes, 1/200-volume of 100% methanol was added to the culture liquid after lapses of 24 hours and 48 hours from starting of the culture. At this time, the system was brought into a closed system after 24 hours from start of the culturing. After end of the culture, the cells and a culture supernatant were collected by centrifugal separation.

The cells were crushed by a glass bead method (manual of Invitrogen No. 25-0043) and a supernatant was obtained. A pentane extract of the supernatant was analyzed by gas chromatography, and β-phellandrene was detected.

The culture supernatant was also extracted with pentane. The extracted fraction was analyzed by gas chromatography, and β-phellandrene was detected. Also the gas phase fraction was analyzed, and β-phellandrene was detected in the gas phase.

On the other hand, in the control recombinant yeast GS115 into which only pPIC3.5K vector was introduced (prepared in Example 3), β-phellandrene was not detected in any of the cells, the culture supernatant, and the gas phase.

These reveal that β-phellandrene can be produced by culturing the recombinant yeast into which GPP synthase gene from *Arabidopsis thaliana* and β-phellandrene synthase gene from lavender were introduced. The produced β-phellandrene was collectible from the cells, the culture supernatant, and the gas phase.

Example 5

In the present example, a recombinant *E. coli* into which NPP synthase gene from tomato and β-phellandrene synthase gene from lavender were introduced was prepared, and the recombinant *E. coli* was cultured, and generation of phellandrene was confirmed and a by-product was identified.

β-phellandrene synthase gene from lavender was cut out by cutting pACLPD prepared in Example 2 with NcoI and EcoRI, and introduced into a NcoI-EcoRI site of pCOLA-Duet-1 (available from Novagen) to construct pCODLFS. On the other hand, using pT21TNPP prepared in Example 1 as a template, PCR was conducted by using primers of SEQ ID NO: 25 and SEQ ID NO: 26 to amplify NPP synthase gene from tomato. The amplified fragment was cut with NdeI and KpnI, and introduced into the NdeI-KpnI site of pCODLFS, to construct coexpression vector pCOLDFSNS. The pCOLDFSNS was introduced into Rosetta2 (DE3) to obtain a recombinant *E. coli* ROFSNS that co-expresses β-phellandrene synthase from lavender and NPP synthase from tomato. As a control *E. coli*, a recombinant *E. coli* ROCOLA having only pCOLA Duet-1 was also prepared.

Figure 1B:
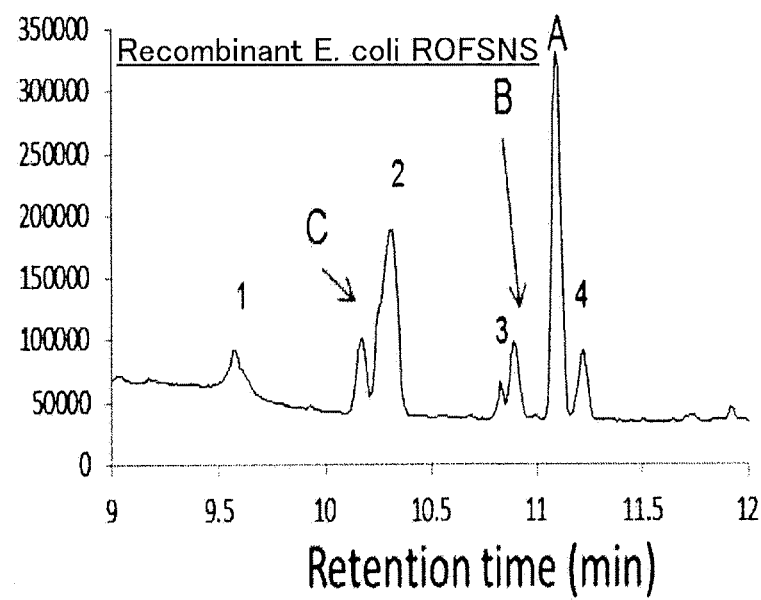
Figure 2A:
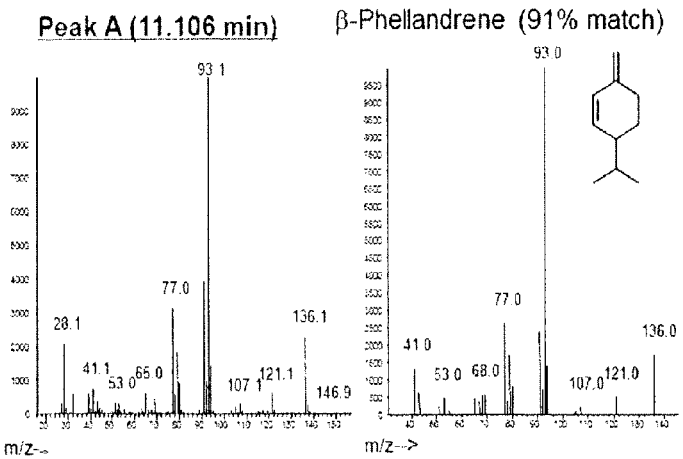
Figure 2B:
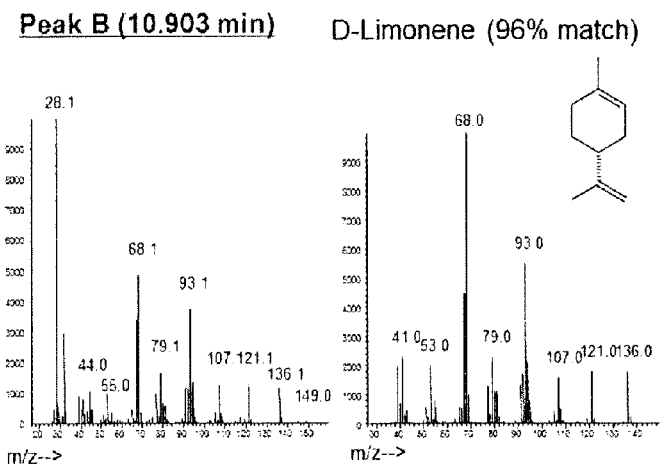
Figure 2C:
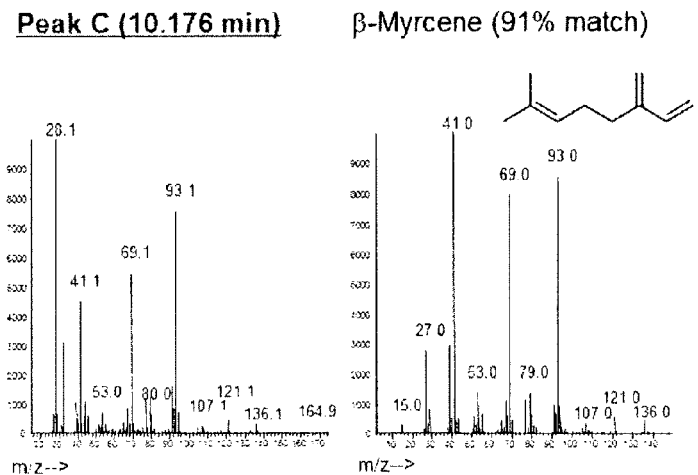

The recombinant *E. coli* ROFSNS and ROCOLA were cultured in a 2×YT medium (1.6% (w/v) Bacto Tripton, 1% (w/v) Yeast Extract, 0.5% (w/v) NaCl) containing 34 μg/mL of chloramphenicol and 15 μg/mL of kanamycin at 18° C., 110 rpm (swing) in a closed system for 24 hours. After end of the culture, the gas phase fraction was analyzed by GC-MS. As shown in FIGS. 1A and 1B, in ROFSNS, β-phellandrene was detected (peak A), and peaks B and C that seem to be by-products were also detected. On the other hand, in ROCOLA, these peaks were not detected. Identification of each peak revealed that small amounts of limonene (peak B) and myrcene (peak C) were generated as by-products in addition to β-phellandrene which is a principal product in the culture gas phase of ROFSNS as shown in FIGS. 2A-2C.

A generation amount of β-phellandrene in the gas phase by ROFSNS was 750 μg per 1 L of the culture liquid.

Example 6

In the present example, a recombinant *E. coli* into which mevalonate pathway gene from *actinomyces*, NPP synthase gene from tomato, and β-phellandrene synthase gene from lavender were introduced was prepared, and the recombinant *E. coli* was cultured to produce β-phellandrene.

Using genome DNA of *Streptomyces griseolosporeus* (*Kitasatospora griseola*) as a template, PCR using primers represented by SEQ ID NO: 27 and SEQ ID NO: 28 was conducted to amplify a nucleic acid encoding mevalonate pathway enzymes of *S. griseolosporeus* (SEQ ID NO: 29). This nucleic acid contains a gene cluster encoding mevalonate kinase, mevalonate diphosphate decarboxylase, phosphomevalonate kinase, IPP isomerase, HMG-CoA (3-hydroxy-3-methylglutaryl coenzyme A) reductase (HMGR), and HMG-CoA synthase. The obtained amplified DNA fragment was cloned into pT7-Blue T vector to construct pT7SMV.

A gene fragment collected from the vector pT7SMV by cutting with NcoI and EcoRI was introduced into a NcoI-EcoRI site of pCOLA Duet-1 (available from Novagen) to construct pCSMV.

Into the NdeI-KpnI site of pCSMV, a synthetic nucleic acid of tomato NPP synthase gene, lavender β-phellandrene synthase gene operon represented by SEQ ID NO: 30 was introduced to construct pCSMVNSFS including *actinomyces* mevalonate pathway gene, tomato NPP synthase gene, and lavender β-phellandrene synthase gene. The expression vector pCSMVNSFS was introduced into *E. coli* Rosetta2 (DE3) to obtain a recombinant *E. coli* ROSMVNSFS.

The recombinant *E. coli* ROSMVNSFS was cultured in a 2×YT medium (1.6% (w/v) Bacto Tripton, 1% (w/v) Yeast Extract, 0.5% (w/v) NaCl) containing 34 μg/mL of chloramphenicol and 15 μg/mL of kanamycin at 18° C., 110 rpm (swing) in a closed system for 24 hours. After end of the culture, the gas phase fraction was analyzed by gas chromatography and β-phellandrene was detected. A generation amount of β-phellandrene in the gas phase was 8.5 mg per 1 L of the culture liquid.

These results and the generation amount of β-phellandrene in Example 5 reveal that the production amount of β-phellandrene can be increased by further introducing *actinomyces* MVA pathway gene.

The invention claimed is:

1. A recombinant *Escherichia coli* (*E. coli*) or *Pichia* yeast cell capable of producing β-phellandrene, prepared by introducing at least one nucleic acid selected from the group consisting of a nucleic acid encoding geranyl pyrophosphate synthase and a nucleic acid encoding neryl pyrophosphate synthase, and a nucleic acid encoding β-phellandrene synthase into a host cell in such a manner that these nucleic acids are expressed in the host cell, wherein the nucleic acid encoding geranyl pyrophosphate synthase encodes the following protein (a), (b) or (c):
(a) protein consisting of the amino acid sequence of SEQ ID NO:2,
(b) protein consisting of the amino acid sequence of SEQ ID NO:2 in which 1 to 20 amino acids are deleted, substituted or added in the amino acid sequence, and having geranyl pyrophosphate synthase activity, or
(c) protein consisting of an amino acid sequence having a homology of 90% or more with SEQ ID NO:2, and having geranyl pyrophosphate synthase activity, wherein the nucleic acid encoding neryl pyrophosphate synthase encodes the following protein (d), (e) or (f):
(d) protein consisting of the amino acid sequence of SEQ ID NO:4,
(e) protein consisting of the amino acid sequence of SEQ ID NO:4 in which 1 to 20 amino acids are deleted, substituted or added in the amino acid sequence, and having neryl pyrophosphate synthase activity, or
(f) protein consisting of an amino acid sequence having a homology of 90% or more with SEQ ID NO:4, and having neryl pyrophosphate synthase activity, and wherein the nucleic acid encoding β-phellandrene synthase encodes the following protein (g), (h) or (i):
(g) protein consisting of the amino acid sequence of SEQ ID NO:6 or 8,
(h) protein consisting of the amino acid sequence of SEQ ID NO:6 or 8 in which 1 to 20 amino acids are deleted, substituted or added in the amino acid sequence, and having β-phellandrene synthase activity, or
(i) protein consisting of an amino acid sequence having a homology of 90% or more with SEQ ID NO:6 or 8, and having β-phellandrene synthase activity, and wherein 10 mg or more of β-phellandrene can be produced per 1 g of wet cells of the recombinant cell.

2. The recombinant *E. coli* or *Pichia* yeast cell according to claim 1, wherein the host cell does not have methane monooxygenase.

3. The recombinant *E. coli* or *Pichia* yeast cell according to claim 2, wherein the host cell is *Escherichia coli* or yeast.

4. The recombinant *E. coli* or *Pichia* yeast cell according to claim 1, wherein a nucleic acid encoding an enzyme group including acetyl CoA acetyltransferase, HMG-CoA synthase, HMG-CoA reductase, mevalonate kinase, 5-phosphomevalonate kinase, diphosphomevalonate decarboxylase, and isopentenyl diphosphate isomerase acting in a mevalonate pathway of isopentenyl diphosphate is further introduced, and the nucleic acid is expressed in the host cell.

5. The recombinant *E. coli* or *Pichia* yeast cell according to claim 4, wherein the mevalonate pathway is a mevalonate pathway of yeast or *actinomyces*.

6. A method for producing β-phellandrene by culturing the recombinant *E. coli* or *Pichia* yeast cell according to claim 1 to produce β-phellandrene in the recombinant *E. coli* or *Pichia* yeast cell.

7. The method according to claim 6, wherein 10 mg or more of β-phellandrene is produced per 1 g of wet cells of the recombinant *E. coli* or *Pichia* yeast cell.

8. The method according to claim 6, wherein β-phellandrene released outside the recombinant *E. coli* or *Pichia* yeast cell is collected.

9. The method according to claim 6, wherein β-phellandrene is collected from a gas phase of a culture system of the recombinant *E. coli* or *Pichia* yeast cell.

10. The recombinant *E. coli* or *Pichia* yeast cell according to claim 3, wherein a nucleic acid encoding an enzyme group including acetyl CoA acetyltransferase, HMG-CoA synthase, HMG-CoA reductase, mevalonate kinase, 5-phosphomevalonate kinase, diphosphomevalonate decarboxylase, and isopentenyl diphosphate isomerase acting in a mevalonate pathway of isopentenyl diphosphate is further introduced, and the nucleic acid is expressed in the host cell.

11. The recombinant *E. coli* or *Pichia* yeast cell according to claim 10, wherein the mevalonate pathway is a mevalonate pathway of yeast or *actinomyces*.

12. A method for producing β-phellandrene by culturing the recombinant *E. coli* or *Pichia* yeast cell according to claim 3 to produce β-phellandrene in the recombinant *E. coli* or *Pichia* yeast cell.

13. A method for producing β-phellandrene by culturing the recombinant *E. coli* or *Pichia* yeast cell according to claim 4 to produce β-phellandrene in the recombinant *E. coli* or *Pichia* yeast cell.

14. A method for producing β-phellandrene by culturing the recombinant *E. coli* or *Pichia* yeast cell according to claim 10 to produce β-phellandrene in the recombinant *E. coli* or *Pichia* yeast cell.

* * * * *